(12) United States Patent
Goméz et al.

(10) Patent No.: US 8,492,099 B2
(45) Date of Patent: Jul. 23, 2013

(54) METHOD OF MEASURING ENZYMATIC ACTIVITY OF ADSORBED ALLERGENIC ENZYME

(75) Inventors: Maria Mercedes Ferreras Goméz, Kgs. Lyngby (DK); Hans-Henrik Ipsen, Hillrod (DK); Morten Jonas Maltesen, Copenhagen (DK); Rasmus Linnemann Krogh, Kgs. Lyngby (DK)

(73) Assignee: Alk-Abello A/S, Horsholm (DK)

( * ) Notice: Subject to any disclaimer, the term of this patent is extended or adjusted under 35 U.S.C. 154(b) by 584 days.

(21) Appl. No.: 12/094,746

(22) PCT Filed: Nov. 23, 2006

(86) PCT No.: PCT/DK2006/000656
§ 371 (c)(1),
(2), (4) Date: May 22, 2008

(87) PCT Pub. No.: WO2007/059776
PCT Pub. Date: May 31, 2007

(65) Prior Publication Data
US 2009/0258377 A1    Oct. 15, 2009

Related U.S. Application Data

(60) Provisional application No. 60/739,408, filed on Nov. 25, 2005.

(30) Foreign Application Priority Data

Nov. 24, 2005    (DK) .................................. 2005 01655

(51) Int. Cl.
*G01N 33/53*    (2006.01)
(52) U.S. Cl.
USPC ......................................... 435/7.1; 435/7.72
(58) Field of Classification Search
None
See application file for complete search history.

(56) References Cited

U.S. PATENT DOCUMENTS

2005/0069868 A1* 3/2005 Wurtzen et al. .................. 435/5

FOREIGN PATENT DOCUMENTS

| EP | 0 377 229 A1 | 7/1990 |
| WO | WO-99/25823 A2 | 5/1999 |
| WO | WO-2005/022157 A1 | 3/2005 |

OTHER PUBLICATIONS

Kuby et al. 'Immunology.' Fourth Edition, Chapter 18: 449-465.*
Morrow et al. 'Regulatory Aspects of Allergen Vaccines in the US.' Clinical Reviews in Allergy and Immunology. 21:141-152, 2001.*
King et al. 'The isolation and characterization of a novel collagenolytic serine protease allergen (Der p 9) from the dust mite Dermatophagoides pteronyssinus.' J Allergy Clin Immunol. 98:739-47, 1996.*
Shulz et al. 'Der p 1, a major allergen of the house dust mite, proteolytically cleaves the low-affinity receptor for human IgE (CD23).' Eur. J. Immunol. 25: 3191-3194, 1995.*
Sepelyak et al. 'Adsorption of Pepsin by Aluminum Hydroxide II: Pepsin Inactivation.' Journal of Pharmaceutical Sciences 73(11):1517-1522, 1984.*
Nail et al. 'Structure of Aluminum Hydroxide Gel I: Initial Precipitate.' Journal of Pharmaceutical Sciences 65(8):1188-1191, 1976.*
Kuby et al. 'Immunology.' Fourth Edition, Chapter 18: 449-465, 2000.*
Chambers Louise et al: "Enzymatically active papain preferentially induces an allergic response in mice" Biochemical and Biophysical Research Communications, vol. 253, No. 3, Dec. 30, 1998, pp. 837-840.
Jacquet et al: "Vaccination with the recombinant allergen ProDer p. 1 complexed with the cationic lipid DiC14-amidine prevents allergic responses to house dust mite" Molecular Therapy, Academic Press, San Diego, CA., US, vol. 11, No. 6, Jun. 2005, pp. 960-968.
Sepelyak et al., Journal of Pharmaceutical Sciences, vol. 73, No. 11, Nov. 1984, pp. 1517-1522.
Jones et al., The Journal of Biological Chemistry, vol. 280, No. 14, Apr. 8, 2005, pp. 13406-13414.
Houen et al., Journal of Immunological Methods, vol. 200, (1997) pp. 99-105.
John et al., Clinical and Experimental Allergy, vol. 30, 2000, pp. 784-793.
Kildsgaard et al., Official Journal of the European Academy of Allergology and Clinical Immunology, Supplement 73, vol. 57, 2002, p. 52.
Jacquet et al., Clinical and Experimental Allergy, vol. 30, 2000, pp. 677-684.

* cited by examiner

*Primary Examiner* — Nora Rooney
(74) *Attorney, Agent, or Firm* — Birch, Stewart, Kolasch & Birch, LLP

(57) ABSTRACT

The invention relates to a method of measuring the immunological activity of a vaccine preparation in the form of a mixture of one or more allergenic enzyme(s) and an oxygen-containing metal salt adjuvant, wherein the mixture comprises a liquid phase and a solid phase, and wherein at least a part of the allergenic enzyme(s) is adsorbed to the solid phase, the method comprising the steps of measuring the enzymatic activity of the mixture in an enzyme activity assay, and using the measurement obtained as an indication of the immunological activity of the vaccine preparation, or using the measurement obtained for quantifying the amount of allergenic enzyme.

29 Claims, 13 Drawing Sheets

METHOD OF MEASURING ENZYMATIC ACTIVITY OF ADSORBED ALLERGENIC ENZYME

TECHNICAL FIELD

The present invention relates to an in vitro method of measuring the enzymatic activity of one or more allergenic enzyme(s) in a vaccine preparation and thereby obtaining an indication of the immunological activity and/or a quantification of the amount of the allergenic enzyme in the vaccine preparation.

BACKGROUND OF THE INVENTION

The interaction of proteins with surfaces is a widely recognized phenomenon of both physiological and technological significance. An important example is the adsorption of protein allergens to the adjuvant aluminum hydroxide in allergy vaccines. An adjuvant is a compound that acts by enhancing the immune response upon vaccination. The adjuvant effect of aluminium hydroxide has been heavily investigated and numerous theories regarding the mechanism have been proposed.

Allergy vaccines for e.g. subcutaneous injection may be prepared by mixing an aqueous solution of an allergen and a solid phase carrier, e.g. aluminium hydroxide gel, to produce a mixture, wherein at least a part of the allergen is adsorbed to the solid phase and part of or none of the allergen is in the liquid phase. The solid phase carrier may serve as an adjuvant, i.e. it potentiates the immune response of the allergen, although the mechanism of the potentiation is not always fully understood. Also, the mechanism and nature of the adsorption of the allergen to the solid phase carrier is not always fully understood and may depend strongly on the type of allergen involved. Theoretically, however, the adsorption to aluminium hydroxide gels partly involves electrostatic forces. For proteins, it is believed that the phosphate groups of phosphorylated proteins also interact with the aluminium hydroxide gel and possibly to some extent replaces the hydroxide groups in the gel structure.

The protein adsorption capacity of aluminium hydroxide has been studied intensively with the model proteins ovalbumin (OA) and bovine serum albumin (BSA). Recently, studies concerning the structural impact of adsorption of protein to aluminium hydroxide have been carried out. Emission fluorescence measurements together with differential scanning calorimetry indicate that major structural alterations occur upon adsorption of OA and BSA to aluminium hydroxide (Jones et al., Effects of Adsorption to Aluminium Salt Adjuvants on the Structure and Stability of Model Protein Antigens, *The Journal of Biological Chemistry*, Vol, 280, pp. 13406-13414, 2005). Another study on the contrary indicates that the presence of aluminium hydroxide in an ELISA experiment helped maintaining OA in the native conformation (Houen et al., A Non-denaturing Enzyme Linked Immunosorbent Assay With Protein Preadsorbed Onto Aluminium Hydroxide, *Journal of Immunological Methods*, Vol. 200, pp. 99-105, 1997). OA adsorbed to aluminium hydroxide before transfer to the plastic surface of the well of a micro titer plate, maintained its ability to bind monoclonal antibodies raised towards the native form of OA. On the contrary OA not pre-incubated with aluminium hydroxide bound to monoclonal antibodies raised against heat denatured albumin. However, these techniques do not give any information on individual proteins present in a mixture of proteins.

The effect of aluminium hydroxide on structure and stability of allergens is important from several perspectives. Conformational epitopes may be lost during adsorption and immunogenicity may be altered as a consequence of storage over longer period of time.

The degree of adsorption varies with the nature of the specific allergen in question. In the case of an allergen in the form of an extract of a biological material, e.g. an extract of grass pollen allergens, the extract contains a number of different ions and molecules, which potentially interferes with the bonding of the allergens to the solid phase carrier.

The house dust mite (HDM) *Dermatophagoides pteronyssinus* is a major source of inhaled allergens. The protein allergens Der p 1 and Der p 2 are considered to be the two most potent allergens of the Der p allergens. The structure and enzymatic activity of Der p 1 has been well characterized. Several in vitro studies suggest that the cysteine protease activity of Der p 1 enhances the potency of the allergen e.g. by cleaving tight junction proteins in the lung epithelial and cleaving CD23 (low affinity IgE receptor) on human B-cells (Jacquet et al., Biochemical and Immunological Characterization of a Recombinant Precursor form of the House Dust Mite Allergen Der p 1 produced by *Drosophila* cells, *Clinical and Experimental Allergy*, Vol. 30, pp. 784-793, 2000). HDM vaccines based on aluminium hydroxide adjuvant contain purified HDM extract as an active pharmaceutical ingredient (API).

The allergenic activity and the potential for inducing allergic reactions may be tested for example by intradermal injection in sensitised animals, and by measurement of the change of various symptoms (Kildsgaard et al., Assessment of the in vivo allergenic potency of new allergy vaccines by intradermal testing in sensitised mice, Clinical Immunology and Allergy in Medicine, Proceedings of the $21^{st}$ EAACI Congress 2002, Naples, Italy). However, such in vivo methods are laborious and time-consuming, and they necessitate the use of test animals, which is undesirable.

Up to now it has been common practise to evaluate the immunological activity of a vaccine in vitro on the basis of a measurement of the immunological activity of the solution of allergen used for the preparation of the ready-to-use solid phase carrier vaccine.

WO2005/022157 discloses an in vitro method of evaluating the immunological activity of a vaccine preparation in the form of a mixture of a molecular antigen and a carrier, wherein the mixture comprises a liquid phase and a solid phase, to which at least a part of the antigen is attached, the method comprising the steps of i) subjecting the vaccine to a measurement of the immunological activity selected from the group consisting of a) antibody binding capacity using an immunoassay employing an antigen-specific antibody bound to an antibody solid phase, b) ability to activate effector cells and c) potential for inducing anaphylaxis; and ii) using the measurement results to evaluate the immunological activity of the vaccine.

The nature of allergen adsorption to oxygen-containing metal salt adjuvants is very complex and largely unknown, and is also expected to vary among different allergens and different oxygen-containing metal salts. The object of the present invention is to provide a new in vitro method of evaluating and quantifying the immunological activity of allergy vaccine preparations based on oxygen-containing metal salt adjuvants, such as ready-to-use vaccines.

SUMMARY OF THE INVENTION

According to one aspect of the invention, a method of measuring the immunological activity of a vaccine preparation in the form of a mixture of one or more allergenic enzyme(s) and an oxygen-containing metal salt adjuvant, wherein the mixture comprises a liquid phase and a solid phase, and wherein at least a part of the allergenic enzyme(s) is adsorbed to the solid phase, the method comprising the steps of measuring the enzymatic activity of the mixture in an enzyme activity assay, and using the measurement obtained as an indication of the immunological activity of the vaccine preparation, is provided.

According to a further aspect of the invention, a method for quantification of the amount of allergenic enzyme in a vaccine preparation in the form of a mixture of one or more allergenic enzyme(s) and an oxygen-containing metal salt adjuvant, wherein the mixture comprises a liquid phase and a solid phase, and wherein at least a part of the allergenic enzyme(s) is adsorbed to the solid phase, the method comprising the steps of measuring the enzymatic activity of the mixture in an enzyme activity assay, and using the measurement obtained for quantifying the amount of allergenic enzyme, is provided.

SHORT DESCRIPTION OF THE FIGURES

DEFINITIONS

Figure 1:
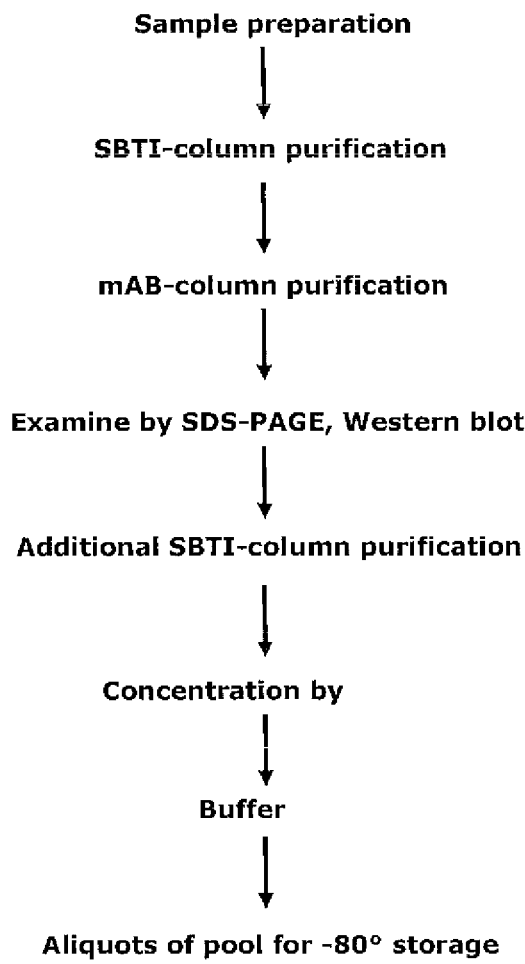
FIG. 1 shows a flow-scheme of the purification of Der p 1.

The expression "in vitro method" as used herein means a method, which may be carried out outside a living organism.

The expression "immunological activity" as used herein means any allergen-specific response of the immune system, including immunoglobulin-mediated immune responses.

The expressions "solid phase" and "liquid phase" of a vaccine preparation as used herein mean the phases resulting from a separation process of a suspension of the oxygen-containing metal salt adjuvant in a liquid solvent e.g. water into a solid phase and a liquid phase, the separation process being e.g. centrifugation, extraction or simple sedimentation.

The expression "adsorbed" as used herein means any non-covalent attachment, coupling, adherence or bonding, including adsorption by electrostatic forces.

DETAILED DESCRIPTION OF THE INVENTION

The present invention relates to an in vitro method of measuring the enzymatic activity of an allergenic enzyme and thereby obtaining an indication of the immunological activity and/or a quantification of the amount of an allergenic enzyme in a vaccine preparation.

In one aspect the invention thus provides a method of measuring the immunological activity of a vaccine preparation in the form of a mixture of one or more allergenic enzyme(s) and an oxygen-containing metal salt adjuvant, wherein the mixture comprises a liquid phase and a solid phase, and wherein at least a part of the allergenic enzyme(s) is adsorbed to the solid phase, the method comprising the steps of measuring the enzymatic activity of the mixture in an enzyme activity assay, and using the measurement obtained as an indication of the immunological activity of the vaccine preparation.

In one aspect of the invention, the term "at least a part of" refers to that at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85% or at least 90% of the allergenic enzymes are adsorbed to the solid phase.

In one aspect of the invention, the immunological activity is the ability of the vaccine preparation to elicit an immune response mediated by an allergen-specific immunoglobulin, including any class, sub-class or combination thereof, including IgA, IgA1, IgA2, IgD, IgE, IgG, IgG1, IgG2, IgG3, IgG4, IgM, in particular IgG and/or IgE.

Although aluminium hydroxide is the most commonly used adjuvant in vaccines, what happens to the allergens when adsorbed to the surface thereof has never been fully characterized. An understanding of how adsorption to aluminium hydroxide affects the structure and activity of allergens is essential to their use in vaccines as well as to the understanding of the mechanism of adjuvanted immune stimulation.

Enzymatic activity is in general directly related to the structure of the enzyme. If the structure is altered, e.g. by exposure to heat or acid conditions, activity is likely to be affected. A population of homogenous proteins can be described by the following simplified two-state equilibrium:

$$N \rightleftharpoons D, \quad K_{D-N} = \frac{[D]}{[N]} = \frac{k_u}{k_f}$$

where N is the protein in the native form, D is the denatured form, $k_u$ and $k_f$ are the rate constants from the unfolding and re-folding kinetics respectively. Between the native and the denatured form a number of intermediate transition states may occur. From this simple model, the definition of denaturation can be stated as any temporary or permanent change in the three-dimensional structure of a protein. Thus when changing the physiochemical properties of the surrounding environment a change of the free energy landscape representing the configuration space available to the protein could occur dependent on how persistent the change is.

Electrostatic attraction to any surface of a solid phase can lead to an adsorption of the protein. The adsorption of a protein to a surface may induce conformational changes in the protein thereby shifting the global energy minimum of the protein. In the case of an enzyme this might result in a change of its enzymatic activity. Thus a change in enzyme activity could be a sensitive measure of structural changes resulting from adsorption to a solid phase.

The protein-aluminium hydroxide system has been thoroughly investigated due to the adjuvant effect of aluminium hydroxide. The literature shows that acidic pI proteins bind to aluminium hydroxide, but the effect of binding on enzymatic activity has as far as the present inventors are aware never been investigated.

The present invention is based on the finding that it is possible to perform measurements of enzymatic activity in a vaccine preparation comprising allergenic enzyme(s) and an oxygen-containing metal salt adjuvant.

The present invention is further based on the recognition that the said measurement of the enzymatic activity of the vaccine preparation can be used as an indication of the immunological activity of the vaccine preparation, since a change in enzymatic activity can be linked to a change in the conformation of the enzyme molecule as present in the vaccine preparation, which again is linked to the immunological activity of the vaccine preparation.

The ability to perform this measurement makes it possible to evaluate the impact of the adsorption of the allergen to the oxygen-containing metal salt adjuvant by measuring the enzymatic activity before and after adsorption to the solid phase carrier and thereby obtaining a measurement of the immunological activity after adsorption since as explained above it is expected that a change in the enzymatic activity will have an impact on the immunological activity.

The method according to the invention can also be used to quantify the amount of allergenic enzyme(s) in a vaccine preparation.

A further aspect of the invention thus provides a method for quantification of the amount of allergenic enzyme in a vaccine preparation in the form of a mixture of one or more allergenic enzyme(s) and an oxygen-containing metal salt adjuvant, wherein the mixture comprises a liquid phase and a solid phase, and wherein at least a part of the allergenic enzyme(s) is adsorbed to the solid phase, the method comprising the steps of measuring the enzymatic activity of the mixture in an enzyme activity assay, and using the measurement obtained for quantifying the amount of allergenic enzyme.

In one aspect of the invention, the quantification of the allergenic enzyme is performed by comparing the enzymatic activity measured with a well-characterised standard. In a further aspect of the invention, the quantification of the enzymatic allergen is performed by active site titration. Active site titration requires the use of an inhibitor of that particular enzymatic activity that binds to the enzyme irreversibly or at least with a very high affinity.

Vaccine Preparation

The vaccine preparation subjected to the method of the present invention may be any ready-to-use preparation in the form of a mixture comprising one or more allergenic enzymes and a oxygen-containing metal salt adjuvant, wherein the mixture comprises a liquid phase and a solid phase, to which at least a part of the allergenic enzyme is adsorbed, or any such vaccine preparation for preparing a ready-to-use formulation. The vaccine preparation may further comprise one or more allergens not having an enzymatic activity.

The ready-to-use preparation may be for parenteral administration or for mucosomal administration.

Parenteral administration includes intravenous, intramuscular, intraarticular, subcutaneous, intradermal, epicutaneous/transdermal and intraperitoneal administration. Vaccines for administration via injection may be formulated so as to be suitable for injection by needle or for needleless injection.

Mucosomal administration includes oral, nasal, vaginal, sublingual, ocular, rectal, urinal, intramammal, pulmonal, otolar (i.e. via the ear) or buccal administration.

The vaccine may be in the form of a spray, an aerosol, a mixture, a suspension, a dispersion, an emulsion, a gel, a paste, a syrup, a cream, an ointment, implants (ear, eye, skin, nose, rectal, and vaginal), intramammary preparations, vagitories, suppositories, or uteritories.

Allergenic Enzyme

In the present context the term "allergenic enzyme" is any protein that induces allergic, i.e. IgE mediated reactions upon their repeated exposure to an individual and has an enzymatic activity i.e. being able to catalyze or speeding up a chemical reaction.

Like all catalysts, enzymes work by lowering the activation energy of a reaction, thus allowing the reaction to proceed much faster. Enzymes may speed up reactions by a factor of many thousands. An enzyme, like any catalyst, remains unaltered by the completed reaction and can therefore continue to function. Because enzymes, like all catalysts, do not affect the relative energy between the products and reagents, they do not affect the equilibrium of a reaction. However, the advantage of enzymes compared to most other catalysts is their sterio-, regio- and chemoselectivity and specificity.

Examples of naturally occurring allergens include pollen allergens (tree-, herb, weed-, and grass pollen allergens), insect allergens (inhalant, saliva and venom allergens, e.g. mite allergens, cockroach and midges allergens, hymenopthera venom allergens), animal hair and dandruff allergens (from e.g. dog, cat, horse, rat, mouse etc.), and food allergens. Important pollen allergens from trees, grasses and herbs are such originating from the taxonomic orders of Fagales, Oleales, Pinales and platanaceae including i.a. birch (*Betula*), alder (*Alnus*), hazel (*Corylus*), hornbeam (*Carpinus*) and olive (*Olea*), cedar (*Cryptomeria* and *Juniperus*), Plane tree (*Platanus*), the order of Poales including i.a. grasses of the genera *Lolium, Phleum, Poa, Cynodon, Dactylis, Holcus, Phalaris, Secale*, and *Sorghum*, the orders of Asterales and Urticales including i.a. herbs of the genera *Ambrosia, Artemisia*, and *Parietaria*. Other important inhalation allergens are those from house dust mites (HDM) of the genus *Dermatophagoides* and *Euroglyphus*, storage mite e.g. *Lepidoglyphys, Glycyphagus* and *Tyrophagus*, those from cockroaches, midges and fleas e.g. *Blatella, Periplaneta, Chironomus* and *Ctenocepphalides*, and those from mammals such as cat, dog and horse, venom allergens including such originating from stinging or biting insects such as those from the taxonomic order of Hymenoptera including bees (superfamily Apidae), wasps (superfamily Vespidea), and ants (superfamily Formicoidae). Important inhalation allergens from fungi are i.a. such originating from the genera *Alternaria* and *Cladosporium*.

In one aspect of the invention, the allergenic enzyme(s) is selected from the group consisting of tree pollen allergens, grass pollen allergens, herb pollen allergens, mite allergens, venom allergens, animal hair and dandruff allergens and food allergens. In a further aspect of the invention, the allergenic enzymes(s) is house dust mite allergen(s).

A non-exhaustive list of allergenic enzymes is shown in table 1.

| Enzymatic Activity | Allergen | Organism | |
|---|---|---|---|
| Cysteine proteases | Der p 1 | *Dermatophagoides pteronyssinus* | HDM |
| | Der f 1 | *Dermatophagoides farinae* | HDM |
| | Blo t 1 | *Blomia tropicales* | Mite |
| | Act c 1 | *Actinidia chinensis* | Kiwi |
| | Car p 1 | *Carica papaya* | Papaya |
| Serine proteases | Der p 3 | *Dermatophagoides pteronyssinus* | HDM |
| | Der p 6 | *Dermatophagoides pteronyssinus* | HDM |
| | Der p 9 | *Dermatophagoides pteronyssinus* | HDM |
| | Cla h 9 | *Cladosporium herbarum* | Fungi |
| | Blo t 6 | *Blomia tropicalis* | Mite |
| | Asp fl 13 | *Aspergillus flavus* | Fungi |
| | Asp f 13 | *Aspergillus fumigatus* | Fungi |
| | Asp p 18 | *Aspergillus fumigatus* | Fungi |
| | Tri r 4 | *Trichophyton tonsurans* | Fungi |
| | Rho m 2 | *Rhodotorula mucilaginosa* | Fungi |
| | Epi p 1 | *Epicoccum purpurascens* | Fungi |
| | Api m 7 | *Apis mellifera* | Honey bee |
| | Pol d 4 | *Polistes dominulus* | Wasp |
| | Cuc m 1 | *Cucumis melo* | Muskmelon |
| Metalloproteases | Asp f 5 | *Aspergillus fumigtus* | Fungi |
| Aspartic proteases | Asp f 10 | *Aspergillus fumigatus* | Fungi |
| | Bla g 2 | *Blattella germanica* | German cockroach |
| Enolases | Cyn d 22w | *Cynodon dactylon* | Bermuda grass |
| | Alt a 6 | *Alternaria alternata* | Grass |
| | Cla h 6 | *Cladosporium herbarum* | Grass |
| | Asp f 22w | *Aspergillus fumigatis* | Fungi |
| | Pen c 22w | *Penicillium citrinum* | Fungi |
| | Rho m 1 | *Rhodotorula mucilaginosa* | Fungi |
| Amylases | Der p 4 | *Dermatophagoides pteronyssinus* | HDM |
| | Blo t 4 | *Blomia tropicalis* | Mite |
| | Hor v 16 | *Hordeum vulgare* | Barley |
| | Hor v 17 | *Hordeum vulgare* | Barley |
| Glutathione transferases | Der p 8 | *Dermatophagoides pteronyssinus* | HDM |
| | Bla g 5 | *Blatella germanica* | German cockroach |
| Arginine kinases | Der p 20 | *Dermatophagoides pteronyssinus* | HDM |
| | Pen m 2 | *Penaeus monodon* | Black tiger shrimp |
| Phospholipases | Api m 1 | *Apis mellifera* | Honey bee |
| | Bom p 1 | *Bombus pennsylvanicus* | Bumble bee |
| | Dol m 1 | *Dolochovespula maculata* | White face hornet |
| | Pol a 1 | *Polistes annularries* | Wasp |
| | Vesp c 1 | *Vespa crabo* | European hornet |
| | Ves m 1 | *Vespula maculifrons* | Yellowjacket |
| | Ves v 1 | *Vespula vulgaris* | Yellowjacket |
| Dehydrogenases | Alt a 8 | *Alternaria alternata* | Fungi |
| | Alt a 10 | *Alternaria alternata* | Fungi |
| | Hala f 4 | *Malassezia furfur* | Fungi |

One of the major sources of allergens is HDMs. In 2000 a total of 13 different species of HDMs have been identified in all continents except the Antarctic. HDMs belong to the phylum Arthropoda as does for instance spiders and scorpions. Three species constitute 90% of the HDM fauna, namely *Dermatophagoides pteronyssinus, Dermatophagoides farinae,* and *Euroglyphus maynei*.

For *D. pteronyssinus* the allergens mediating the allergic response are found in the faeces and from the desiccated bodily remains of the *D. pteronyssinus*. 14 different groups of allergens from *D. pteronyssinus* are identified (Table 2). Although not all are completely characterized, size and function of most is established and immunological assays have determined the in vitro IgE reactivity.

As it appears from table 2 several of the HDM's are allergenic enzymes such as e.g. Der p 1, Der p 3, Der p 6 and Der p 9.

TABLE 2

*Dermatophagoides pteronyssinus* allergen groups - molecular weight and function.

| Allergen | Mw (kDa) | Function |
|---|---|---|
| Group 1 | 25 | Cysteine protease |
| Group 2 | 14 | Epithelial secretion |
| Group 3 | 25 | Trypsin |

TABLE 2-continued

Dermatophagoides pteronyssinus allergen groups - molecular weight and function.

| Allergen | Mw (kDa) | Function |
| --- | --- | --- |
| Group 4 | 57 | Amylase |
| Group 5 | 15 | NA |
| Group 6 | 25 | Chymotrypsin |
| Group 7 | 31 | NA |
| Group 8 | 26 | Glutathione-S-transferase |
| Group 9 | 30 | Collagenolytic serine protease |
| Group 10 | 37 | Tropomyosin |
| Group 11 | 92 | Paramyosin |
| Group 12 | 14 | NA |
| Group 13 | 15 | Fatty acid binding protein |
| Group 14 | 189 | Apolipophorin |

NA: Not available

The formal definition of a major allergen is any antigen that binds to human IgE sera in more than 50% of patients in a clinically sensitive group. The HDM allergens Der p 1 and Der p 2 are both major allergens and are considered the most potent of the HDM allergens.

A number of in vitro experiments indicate that the proteolytic activity of Der p 1 could play an essential role in the development of the allergic reaction towards HDM. It is believed that Der p 1 disrupts the tight junctions between the epithelial cells by cleaving occluding and increases the permeability of bronchial mucosa by degrading α-antitrypsin. This could facilitate an increased access to the sub-epithelial antigen presenting cells, which could lead to an increased allergic response. Furthermore Der p 1 cleaves CD23 (the low affinity IgE receptor that regulates the production of IgE) and CD25 (the IL-2 receptor) on the surface of B- and T-cells. This directs the T cell response towards a Th2 response and finally to increased levels of IgE and a more severe allergic response.

Proteolytic enzymes, referred to as proteases or synonymously peptidases, mediate the breakdown of proteins. This is done either by limited proteolysis where a limited number of peptide bonds are cleaved or by unlimited proteolysis where proteins are degraded into their amino acid constituents. Proteolytic enzymes, as most of all other enzymes, are classified by the Enzyme Commission (EC) numbering system with a number indicating function and substrate specificity. The proteolytic enzymes are divided, according to the EC numbering system, into two sub-subclasses, namely exopeptidases and endopeptidases. The later are also referred to as proteinases.

The exopeptidases, e.g. amino- and carboxy peptidase, cleave off single amino acids from either the N- or the C-terminal of the protein, whereas endopeptidases cleave bonds within the protein. For endopeptidases, the particular bond cleaved is dependent on the specificity or the preference towards distinct amino acids in the protein substrate. Thus, one endopeptidase might have a preference towards cleaving peptide bonds neighbouring a bulky hydrophobic residue whereas others prefer long charged residues or even two or more chemically or structurally related residues. The actual structure around the active site of the protease dictates the specificity or preference. The residues around the cleavage site of the substrate are denoted $-P_3-P_2-P_1-P_1'-P_2'-P_3'-$, the stretch $P_1-P_1'$ being the site of cleavage. Similarly, the residues of the protease aligned to the substrate are denoted $-S_3-S_2-S_1-S_1'-S_2'-S_3'-$.

Four different types of endopeptidases have been described. These are the serine proteases, cysteine protease, aspartyl proteases, and metalloproteases. In each case the proteases generate a nucleophile which attacks the peptide carbonyl of the protein substrate.

The cysteine proteases, are hydrolases active towards peptide bonds via a cysteine residue, belong to sub-subclass 3.4.22 in the EC numbering system. 40 cysteine proteases are currently classified in this system, covering enzymes as caspase-1, separase, some cathepsins, and papain (Car p 1). A number of other cysteine protease have been identified and characterized but has not yet been classified in the EC numbering system.

Besides the EC numbering system, proteases are also classified into clans and families on the basis of phylogenetic relationship. That is, their molecular structure and sequence homology. At present the MEROPS database contain detailed information on 1816 different proteases. In this system proteases are annotated by a letter indicating the catalytic type (S, C, T, A, G, M or U. for serine, cysteine, threonine, aspartic, glutamic, metallo- or unknown protease, respectively) followed by an arbitrary number. The cysteine proteases are divided into five clans. By this system, Car p 1 belongs to clan CA, family C1, and is given the name C.01.001, in contrast to 3.4.22.2 in the EC numbering system.

The catalytic residues responsible for the activity of cysteine proteases are well conserved: a cysteine (Cys), a histidine (His), and an asparagine (Asn) constitute the so called catalytic triad. These three residues generate a nucleophilic thiolate anion from the Cys. A thiolate-imidazolium ion pair is generated from the His and the Cys, which attacks the peptide carbonyl of the substrate. The Asn helps orient the imidazolium ion of the His in favourable positions for the various steps of the catalytic mechanism. The catalysis happens in a sequential manner. First the enzyme is temporarily acylated by the protein substrate through the thiolate anion. Second, one part of the protein substrate is cleaved followed by deacylation and the addition of water. Finally the active site residues of the cysteine protease are reconstituted into their original form.

In addition to the catalytic residues, a number of other residues play important roles. A Glutamine (Gln) constitutes part of what is known as the oxyanion hole. This structure helps stabilizing the substrate intermediate transition state during catalysis. A number of hydrophobic residues maintain a nonpolar environment around the Asn, shielding it from external solvent. These are two tryptophans (Trp), two valines (Val) and one phenylalanine (Phe), all conserved residues.

The catalysis performed by cysteine proteases is strongly dependent on a reducing environment, since the reactive cysteine is prone to oxidization. For this reason enzymatic assays with cysteine proteases may be conducted with a reducing agent e.g. dithiothreitol (DTT), free cysteine, or β-mercaptoethanol.

The cysteine protease Car p 1 from the plant *Carica papaya* is the most studied and well understood cysteine protease. Car p 1 is a member of the family C1 cysteine proteases which usually are secreted and produced as inactive pro-forms. Car p 1 consists of a single polypepetide chain of 212 amino acids with three disulfide bridges. The polypeptide chain is folded to form a globular protein constituted by two interacting domains delimiting a cleft between them. The active site residues Cys25 and His159 are located in this cleft on opposite domains. The domain harbouring Cys25 is dominated by α-helical structural motifs whereas the domain harbouring His159 is dominated by β-sheet structural motifs. The third catalytic residue Asn175 is residing in close proximity to His159 in sequence and tertiary structure. Apart from the Cys25 coordinating the carbonyl of the substrate, Asn175 and Gln19 help keeping the substrate in place for catalysis by hydrogen bonding and constitutes the core of the mentioned oxyanion hole. The optimum pH of Car p 1 proteolytic activity is 6.0-7.0.

Der p 1, a major HDM allergen originating from its faeces is also a member of the family C1 cysteine proteases. Although not granted a place in the EC numbering system it has been classified in the MEROPS peptidase database with the number C.01.073. Der p 1 is excreted as a proenzyme in the HDM's gastrointestinal tract and is activated by proteolytic removal of the pro-peptide forming the mature enzyme consisting of 222 amino acids with three disulfide bridges. The open reading frame encodes an 18 amino acid signal peptide in addition to an 80 amino acid pro-peptide. Der p 1 is structurally very similar to Car p 1 and they display an 80% structure homology, despite a sequence homology of 26%. The optimum pH of Der p 1 proteolytic activity is 7.0-8.0.

In one aspect of the invention, the allergenic enzyme(s) is one or more selected from the group consisting of Der p 1, Der p 3, Der p 6 and Der p 9.

In another aspect of the invention, at least one of the allergenic enzyme(s) is a cysteine protease such as Der p 1.

In yet another aspect of the invention, at least one of the allergenic enzyme(s) is a serine protease such as one or more selected from the group consisting of Der p 3, Der p 6 or Der p 9.

In yet another aspect of the invention, the vaccine preparation comprises at least two different species of allergens either originating from the same allergic source or originating from different allergenic sources e.g. mite group 1 and group 3 allergens from different mite.

The allergenic enzyme incorporated into the vaccine preparation may be in the form of an extract, a purified allergen, a modified allergen, a recombinant allergen or a mutant of a recombinant allergen. An allergenic extract may in addition to the allergens contain a number of other ions and molecules. An allergenic extract may naturally contain one or more isoforms of the same allergen, whereas a recombinant allergen typically only represents one isoform of an allergen. The vaccine preparation may further comprise one or more allergens not having an enzymatic activity and/or one or more enzymes not having allergenic activity.

In one aspect of the invention, the allergenic enzymes(s) is in the form of an extract. In another aspect of the invention, the enzymatic activity of a major allergen of the extract is measured.

In yet a further aspect of the invention, the enzymatic activity of one or more allergenic enzymes in a whole extract may be measured.

In another aspect of the invention, the allergen is a recombinant allergen. In a further aspect of the invention, the allergen is a naturally occurring low IgE-binding mutant or a recombinant low IgE-binding mutant.

In a further aspect of the invention, the low IgE binding allergen is an allergen according to WO 99/47680, WO 02/40676 or WO 03/096869.

Enzyme Inhibitors

Enzyme activity can be affected by other molecules such as inhibitors that are molecules that decrease or abolish enzyme activity.

A large number of protease inhibitors, both natural and synthetic, have been described. Inhibitors inactivate the enzyme by different mechanisms e.g. direct covalent modification of the catalytic residues or by shielding the active site for entry of substrate. The first type of mechanism is often represented by small molecules with a reactive group towards catalytic residues thereby irreversibly blocking the activity. An example of such an inhibitor is the specific cysteine protease inhibitor E-64, which covalently binds to the catalytic cysteine through a reactive epoxide group. The latter type of inhibitor is often a macromolecular structure that associates to the enzyme by multiple non-covalent interactions. An example of such an inhibitor is the soybean trypsin inhibitor (SBTI), specific for serine proteases. SBTI is an 190 amino acid naturally occurring protein, which covers the active site cleft and thereby the catalytic residues by hydrogen bonding, electrostatic, and hydrophobic interactions with the surface of the enzyme.

In one aspect of the invention, the vaccine preparation comprises several allergenic enzymes. In order to measure only the activity of one of the allergenic enzymes it might be necessary to use relevant inhibitors depending on the type of enzymatic activity it is desired to inhibit. In a further aspect of the invention, an inhibitor is used to inhibit one or more of the allergenic enzymes(s) in the vaccine preparation.

The use of specific inhibitors for the allergenic enzyme in question are useful to obtain a better characterisation and identification of the enzymatic activity, as well as for the quantification of the amount of active enzyme present in the preparation (by e.g. active site titration). In one aspect of the invention, the cysteine protease inhibitor used is selected from the group consisting of E64 (L-trans-epoxysuccinyl-L-leucylamido (4-guanidino) butane) and other epoxides. In a further aspect of the invention, the inhibitor is E64.

Substrates

In order to be able to measure the enzymatic activity of an allergenic enzyme adsorbed to the solid phase in an enzyme activity assay a substrate should be identified and, such as if needed, a specific inhibitor for the allergenic enzyme in question.

In one aspect of the invention, the substrate in the enzymatic activity assay is specific for the enzyme in question, which means that no other enzymes in the same allergenic source is able to convert this substrate into product. As an example, the substrate Z-Leu-Leu-Glu-MCA is specific for cysteine proteases, e.g. Der p 1, and it is not cleaved by the other proteases known to be present in that allergenic source (HDM extracts), such as the serine proteases Der p 3, Der p 6 or Der p 9. In one aspect of the invention, a substrate specific for an allergenic enzyme is used for measuring the enzymatic activity of the allergenic enzyme. In a further aspect of the invention, the substrate used is Z-LeuLeuGlu-MCA.

Oxygen-Containing Metal Salt Adjuvant

An adjuvant is a compound that acts by enhancing the immune response upon vaccination.

The oxygen-containing metal salt to be used in accordance with the invention may be any oxygen-containing metal salt providing the desired effect when formulated into a delivery system. Examples of such oxygen-containing substances are aluminium hydroxide, aluminium phosphate, aluminium sulphate, potassium aluminium sulphate, calcium phosphate, Maalox (mixture of aluminium hydroxide and magnesium hydroxide), beryllium hydroxide, zinc hydroxide, zinc carbonate, zinc chloride and barium sulphate.

Examples of suitable oxygen-containing metal salts are e.g. those, wherein the cation is selected from Al, K, Ca, Mg, Zn, Ba, Na, Li, B, Be, Fe, Si, Co, Cu, Ni, Ag, Au, and Cr.

The anion of the oxygen-containing compound may be an organic or inorganic anion, or a combination of organic and inorganic anions. Examples of suitable oxygen-containing metal salts are e.g. those, wherein the anion selected from sulphates, hydroxides, phosphates nitrates, iodates, bromates, carbonates, hydrates, acetates, citrates, oxalates, and tartrates, as well as mixed forms thereof. The oxygen-containing metal salts further comprise coordination complexes. A definition of coordination complexes is given in e.g. The Handbook of Chemistry and Physics 56 Ed., Section B, Chapter 7 (1975-76).

Within the present context, the expression "mixed forms" is intended to include combinations of the various anions as well as combinations with e.g. chlorides, and sulphides.

Although the delivery system comprises an oxygen-containing metal salt, it is contemplated that the oxygen could be substituted by another Group VIA atom such as S, Se or Te.

Oxygen-containing metal salts can be characterised by a variety of physical-chemical parameters like adsorption, solubility and dissolution properties, ionic charge measured as the isoelectric point pI (pH where the net charge of the substance is zero for a dissociationable compound), dissociation constants, complex coordination, electronic configurations, valence, bonding orbitals and antibonding orbitals, depot properties, adhesion properties, surface characteristics, particle characteristics, and adjuvanticity.

It is believed that the biologically active substance is adsorbed (or coupled) to the oxygen-containing metal salt, and this adsorption contributes to the efficacy of the vaccine. Several factors may be important or influence the adsorption between the active substance and the oxygen-containing metal salt (see e.g. P. M. Callahan et al., Pharmaceutical Research Vol. 8, No. 7, 851-858 (1991), and Vaccine Design. The Subunit and Adjuvant Approach). These factors include pH, the length of time the adsorption reaction is carried out for, mixing conditions, concentrations of the various components in the vaccines, containers, temperature, storage, buffer and excipients. It has further been found that the adsorption of the active substance may be influenced by the net/overall charge of the metal salt and the charge of the active substance, both of which are pH dependent. A further feature believed to be of importance is the solubility of the oxygen-containing metal salts.

The oxygen-containing metal salt may further have a depot effect. A depot effect means that the active substance will be released gradually from the vaccine. The active substance will thus be retained with the oxygen-containing metal salt (s) and released gradually therefrom. This is believed to have a number of beneficial effects, e.g. prolonged stimulation, beneficial drug release, and protection of the biological interactive substances against environmental conditions. It is further believed that the oxygen-containing metal salt may possess certain entrapment properties, thus retaining the active substance to be delivered.

Another feature of oxygen-containing salts is the protection of the active substance either by maintaining the ideal pH for the active substance in the microenvironment, thus preventing acid degradation, or by protecting the active substance against enzymatic degradation thereby allowing the substance to be delivered.

Furthermore, some of the oxygen-containing metal salts have a buffer capacity. This may result in an in vivo microenvironment within the vaccine formulation, which protects the active substance from the degradable environment. This may e.g. be an advantage in the stomach or intestine where there is a risk of acid and enzymatic degradation, respectively.

Some oxygen-containing metal salts, e.g. aluminium hydroxide, have the form of a gel suspended in a solvent, typically water. When stirred the gel, i.e. the solid phase, will distribute uniformly over the entire volume of the suspension hence enclosing all of the water, i.e. the liquid phase, present. When left to stand or when subjected to a separation process, such as centrifugation, a part of the water will be separated from the gel. The amount of water separated will depend on the separation process used as well as the type and concentration of the oxygen-containing metal salt used.

In one aspect of the invention, the oxygen-containing metal salt is selected from the group consisting of aluminium hydroxide, aluminium phosphate and calcium phosphate.

In one aspect of the invention, the oxygen-containing metal salt is aluminium hydroxide. The molecular formula of aluminium hydroxide is $Al(OH)_3$. This however underestimates the true complexity of the compound. The molecular structural composition is an octahedron. Aluminium is in the centre of the symmetry plane of the bipyramid, hydroxides in the connective intersections and water molecules in all other. The individual octahedron combines yielding macromolecular structures of octahedras. As more octahedras combine the ratio of aluminium to oxygen asymptotically approaches 1:3 as more hydrogen from water is displaced.

The physical appearance of aluminium hydroxide is a gel suspension with decreasing fluidity according to increasing content of aluminium. The gel aggregates and therefore sediments when stored due to its high density, leaving an aqueous phase above it. The typical particle size of an aluminium hydroxide aggregate is in the area of two to three μm. Aluminium hydroxide has a point of zero charge (PZC) of 9.1. The PZC is equivalent to the pI in proteins, which is the pH value where the molecule has an overall net charge of zero. The pI's of Car p 1 is 8.75 and for Der p 1 4.6-6.6 (depending on the different Der p 1 isoforms).

In addition it has been shown that the microenvironment surrounding the aluminium hydroxide adjuvant has a different pH than that of the bulk solution. This is due to the attraction of anions including hydroxyls that form a double layer surrounding the adjuvant particles.

The basis of the adsorption of proteins to aluminium hydroxide is mainly mediated by their difference in charge. A substantial difference in PZC to pI at constant pH is needed in order to establish the electrostatic interactions required for the adsorption. This is supported by the Nernst potential or the surface potential for aluminium hydroxide given by $$\text{Surface potential} = 59 \text{ mV} \cdot (\text{PZC} - \text{pH})$$

Proteins with a pI lower than PZC will be able to bind to aluminium hydroxide. The larger the difference between PZC and pH, the higher is the potential of the aluminium hydroxide adjuvant and the stronger is the electrostatic interaction between aluminium hydroxide and protein given that pI of the protein is lower than the PZC of aluminium hydroxide.

Other interactions including hydrophobic, van der Waals, and hydrogene bonding but are not themselves sufficient to drive the adsorption if no significant difference in charge between the molecules exist. Thus, in theory, Car p 1 should not or at least to low extent, adsorb to aluminium hydroxide, whereas Der p 1 should be adsorbed due to large difference in charge compared to aluminium hydroxide.

Enzyme Activity Assay

The purpose of the enzymatic activity assay is to obtain a progress curve of an enzyme catalyzed reaction. The initial velocity is estimated as the initial rate of product formation or the initial decrease in substrate concentration. This can be obtained in different ways depending on the enzyme reaction the most popular being absorbance, fluorescence or pH change. An enzyme's progress curve is the concentration of product as a function of time. In the present context the term "enzyme activity assay" relates to any appropriate assay depending on the allergenic enzyme to be measured. By the method chosen it should be possible to follow and quantify the consumption of substrate and/or the generation of product by methods that are compatible and not altered by the presence of the solid phase carrier, e.g. by spectroscopic methods like absorbance, fluorescence, FTIR (Fourier Transform Infrared spectrometry), by immunological methods, e.g. ELISA, and the like. Before deciding on a assay it is standard practice for a skilled person within the field to verify that the presence of the solid phase do not interfere with the enzymatic catalysis, with the assay conditions (e.g. by binding the substrate and/or the product, altering the pH conditions, etc), or with the measure method itself, in a way that it affects the measured results as for example exemplified in the examples herein.

In one aspect of the invention, the assay is a fluorescence assay where the product formation is measured over time. The substrate can be made of a synthetic peptide linked to a fluorescent group which is quenched by the peptide, and has relatively low fluorescence intensity while attached to the peptide, such as the cysteine protease substrates Boc-Gln-Ala-Arg-MCA, Z-Leu-Leu-Glu-MCA or Z-Phe-Arg-MCA, where MAC is the fluorescent group. When an enzyme cleaves the bond between the fluorescent group and the peptide sequence the fluorescence increases dramatically. The peptide can be designed to meet the specificity requirements of the enzyme.

When the allergenic enzyme, in one aspect of the invention, is a cysteine protease the active cysteine residue needs to be in its reduced form in order for the protease to be enzymatically active. In this aspect of the invention, the allergenic enzyme is incubated with a reducing agent to activate the allergenic enzyme. It is important that the reducing agent is present in a sufficient concentration so to fully reduce the active site cysteine residue but not in such an excess concentration so to reduce the disulfide bridges of the enzyme.

In one aspect of the invention, the enzymatic activity of the mixture of the liquid phase and the solid phase of the vaccine preparation is measured. In a further aspect of the invention, the vaccine preparation is subjected to a separation process to separate the liquid phase and the solid phase in order to make it possible to measure the enzymatic activity of the solid phase and the liquid phase separately. The separation can be performed by any appropriate method. In one aspect of the invention, the separation process is performed by centrifugation, extraction or simple sedimentation. Depending on the specific enzymatic assay used and the quality of the sample of the solid phase, it can be necessary to use for example buffer solutions in order to obtain an appropriate sample before measuring the enzymatic activity of the allergenic enzymes(s).

In one aspect of the invention, the vaccine preparation is subjected solely to a measurement of the enzymatic activity of allergenic enzyme in the mixture of the liquid phase and the solid phase (measurement 1).

In a further aspect of the invention, the vaccine preparation is subjected solely to a measurement of the enzymatic activity of allergenic enzyme in the liquid phase upon a separation of the liquid phase from the solid phase (measurement 2).

In a further aspect of the invention, the vaccine preparation is subjected solely to a measurement of the enzymatic activity of allergenic enzyme in the solid phase upon a separation of the liquid phase from the solid phase (measurement 3).

In yet a further aspect of the invention, the vaccine preparation is subjected both to a measurement of the enzymatic activity of the mixture of the liquid phase and the solid phase (measurement 1), and to a measurement of enzymatic activity of allergenic enzyme in the liquid phase (measurement 2).

In yet another aspect of the invention, the vaccine preparation is subjected both to a measurement of the enzymatic activity of allergenic enzyme in the liquid phase (measurement 2), and to a measurement of the enzymatic activity of allergenic enzyme in the solid phase (measurement 3).

The distribution of the allergenic enzymes between the liquid phase and the solid phase is a parameter, which is characteristic for each allergenic enzyme, and hence it may serve to characterise the state and the immunological activity of a vaccine preparation. Accordingly, the purpose of the above aspects of the invention involving measurements of the enzymatic activity of various combinations of different phases of the vaccine preparation and/or the whole vaccine preparation is to give additional information about the immunological activity of the vaccine preparation.

In another aspect of the invention, the enzymatic activity of a solution of allergenic enzymes used for preparing the adjuvanted vaccine preparation is measured, and the measurement for the said solution is compared to the measurement obtained for the adjuvanted vaccine preparation in order to evaluate the effect on the immunological activity of the preparation of the adjuvanted vaccine preparation.

In yet another aspect of the invention, the vaccine preparation is subjected to the enzymatic activity measurement immediately after preparation and after one or more periods of storage, and the indication of the immunological activity of the vaccine preparation is based on a comparison of the former and latter measurements.

In another further aspect of the invention, the indication of the immunological activity of the vaccine preparation is based on a comparison of the measurement obtained for the adjuvanted vaccine preparation and prior corresponding measurements of the same type of adjuvanted vaccine preparation or of another type of vaccine preparation.

METHODS AND MATERIALS

Preparation of Aluminium Gel Adjuvant Allergen Vaccines

Lyophilised allergen is dissolved in an aqueous buffer and diluted to a desired concentration. "Alhydrogel" (1.3%) is added to the allergen solution obtained wile stirring, and then sterile water is added. The resulting solution is allowed to stand to the following day, and then buffer is added slowly while stirring to produce the final allergen aluminium hydroxide gel.

Rocket Immune Electrophoresis
Objective

This method was used to quantify a given protein by measuring the propagation of protein-antibody complex after electrophoresis in an agarose gel containing antibodies directed against the protein under investigation.

Theory

This method is based on the mobility of protein-antibody complex in an agarose gel during electrophoresis. The antibodies are incorporated into the agarose gel during polymerization and the sample protein is then applied to the wells. The proteins move according to their electrophoretic mobility encountering the antibodies in the gel and forming complexes. These complexes grow in size as the antigen encounters more and more antibodies thereby limiting the migration through the pores of the gel until no further migration occurs. The complexes are visualized by staining the gel. The area delimited by the complexes is proportional to the amount of protein applied to the well. The quantification is performed relative to an internal standard preparation applied in a dilution series on the same gel.

Apparatuses:
Heated thermostat-controlled waterbath 56-60° C.
Electrophoresis apparatus (2 buffer vessels, 2 electrodes, cooled surface, and chamber)

Power supply, Immuno Power 320, Kebo Lab A/S
Hot air blower, Team International HL2
Materials and Reagents:
Glass plate: 7×10 cm
Paper wicks: filter paper, standard size: 21×10 cm, Watman
Buffer for Electrode Vessels and Agarose Gel:
0.1M 5,5-diethylbarbituric acid, Veronal, 0.40M Tris, Sigma, 2 mM Calcium lactate, Purum
Agarose Gel Containing Antibodies:
1% (w/v) Agarose, type HAS, Litex
Antibody: Rb-a-Derp1, ALK-Abelló A/S
Staining Solution:
6 mM Coomasie Brilliant Blue R-250, Pierce, 10% acetic acid, Bie & Berntsen in 43.2% ethanol
Destaining Solution:
10% acetic acid, Bie & Berntsen in 43.2% ethanol
Experimental Procedure A glass plate was placed on a leveled surface and cleaned with ethanol. 11 mL agarose was pipetted into a test tube in a 56° C. water bath, 15 µL antibody was added, and the solution was mixed gently by inversion. The agarose was poured onto the glass plate carefully avoiding formation of air bubbles. After gelation a series of wells were punched 1.5 cm from the lower edge of the plate. The plate was placed on the cooled surface of the electrophoresis apparatus. Connecting bridges of 5 layers of filter paper were established and the voltage across the gel adjusted to 2V/cm. 10 µL of sample was applied to the wells. Another glass plate was placed on top of the connecting bridges filter paper to avoid water condensation on the gel and electrophoresis was continued overnight.

After the electrophoresis was conducted the glass plate was placed on filter paper and the wells filled with distilled water. Then the gel was covered with wet filter paper and pressed under several layers of dry filter paper, a thick glass plate and a 3-4 kg load. After ten minutes the procedure was repeated. The plate was then placed in a container with 0.1M NaCl for 15-30 minutes followed by pressing as described above. After this the plate was dried in a stream of hot air and plates were stained for 5 min in Coomassie staining solution.

The plate was immersed in distilled water for a few seconds in order to remove excess staining solution. Finally the plate was de-stained for 2 minutes in successive baths until the desired de-staining was reached. The plate was dried with hot air and digitalization of the gel was done by the Gel-Pro Analyzer 3.1 software.

Der p 1 Purification
Objective

The purpose is the purification of Der p 1 from *D. pteronyssinus* extract.

Theory

The purification of Der p 1 involves several steps. Application of two types of affinity chromatographic steps leads to the purified Der p 1. The first chromatography was performed on an SBTI agarose column. The purpose of this step is the removal of contaminating serine proteases present in the extract, rendering a more stable extract.

The second step in the purification is performed on a 4C1B8 sepharose column. 4C1B8 is a mouse monoclonal antibody specific for Der p 1 (from Martin Chapman). The Der p 1 is eluted by applying a pH gradient.

Flow-scheme of the purification is shown in FIG. 1.

An additional purification on an SBTI-column is performed in order to completely remove traces of the Der p 3 serine protease that co-purifies with Der p 1 in the previous step. The fractions containing Der p 1 were collected and concentrated by ultrafiltration Apparatuses:
ÄKTA explorer FPLC system, Amersham Biosciences
Sorval RC 3B Plus centrifuge, Du Pont
Materials and Reagents:
Affinity Purification:
Columns: SBTI-agarose Der p 1 column (SBTI agarose), column volume (CV) 1 mL
CNBr-sepharose 4C1B8 mAb Der p 1 column (4C1B8 sepharose), CV 5 mL
House dust mite extract from *D. pteronyssinus* Buffers for chromatographic purification:
A11: Phosphate buffered saline (PBS), Bie & Berntsen
A2: PBS, 0.5 M NaCl, Merck
B1: 0.1 M Glycine pH 11, Sigma, 0.5 M NaCl, Merck
Protein Concentration:
Amicon Ultra-15 mL centrifugal filter devices, Millipore.
Buffer Exchange:
PD 10 Desalting column, Amersham Biosciences
Experimental Procedure
Sample Preparation 120 mg of Der p extract was dissolved in 10 mL buffer A11. The sample was filtered with a 0.22 µm low protein binding filter. In order to reduce possible proteolysis of Der p 1 all operations were carried out at 5° C. All buffers used were cooled to 5° C. as well.

SBTI agarose column affinity chromatography

The SBTI agarose column was equilibrated with buffer A11 and 5 mL of the prepared sample was injected onto the column. 50 µL samples of fractions were taken out for further investigation and frozen separately. The fractions of the flow-through containing Der p 1 were pooled for further purification.

4C1B8 Sepharose Column Affinity Chromatography

The column was equilibrated with buffer A11 and 5 mL of sample (SBTI-agarose purified pool) was injected onto the column. The non-specifically bound material was eluted with buffer A2. Afterwards, Der p 1 was eluted with a gradient to buffer B1. 800 mM Phosphate buffer, pH 7, was pipetted in the collection tubes (200 µL/mL fraction) destined for the collection of Der p 1 in order to neutralize the alkaline eluate. 50 µL samples of fractions were removed and frozen separately for further investigation. Fractions of the elution peak were pooled and frozen. The fractions containing Der p 1 were pooled and subjected to a second chromatography on SBTI agarose, under the same conditions described earlier.

Post Purification Processes

The pool, around 140 mL, from the second SBTI-column purification was concentrated by ultra filtration, using Amicon Altra-15 15 mL centrifugal filters. The filters were washed with PBS buffer and the pooled Der p 1 was centrifuged at 3,500 rpm for 15 minutes reducing the volume to 5 mL.

The buffer was changed to 50 mM Tris pH 7 using the PD-10 Desalting column packed with Sephadex G-25 designed to separate high (MW>5000) from low molecular weight substances (MW<1000).

Absorbance
Objectives

This method is used to evaluate total protein concentration

Theory

The aromatic amino acids tryptophan, tyrosine and phenylalanine absorb ultraviolet light. However only tryptophan and tyrosine absorb at 280 nm and tryptophan absorbs 5 times more light than tyrosine. This is due to the n→n* transition in the indole ring of tryptophan where phenylalanine and tyrosine contains a phenyl group. The absorbance of a protein is linearly correlated with the amount of tryptophan and tyrosine in the protein, the length of the light path and the concentration of protein. This relationship is named Lambert-Beer's law and is given by:

$$A = \epsilon \cdot l \cdot c$$

where A is the absorbance, ε is the molar absorption coefficient for the protein (determined by the amount of tryptophan and tyrosine in the protein) l is the length of the light path and c is the protein concentration. Thus from an absorbance measurement the concentration of protein can be estimated if the molar absorptivity coefficient is known.

Apparatuses
Lambda 800 UV/VIS Spectrometer, PerkinElmer™ 100-QS, quartz cuvette, path length 1 cm, Hellma®
Materials and Reagents
50 mM Bis-Tris pH 6.5, Sigma
50 mM Tris pH 7.0, Sigma
50 mM phosphate buffer pH 7.0, Merck
2% Helmanex solution, Hellma Experimental Procedure The spectrophotometer was turned on 30 min prior to use for a warm up period. The wavelength of the spectrophotometer was set to 280 nm and the instrument was zeroed to a blank sample containing the matrix of the true sample. The quartz cuvette was washed first with a 2% Helmanex solution and then 4 times with MQ water and afterwards dried with high pressure air. After air drying, the outside of the cuvette was robbed with lens cleaning tissue. This procedure was performed between each sample measurement. After cleaning the cuvette 20 µL of sample was transferred to the cuvette and the absorbance was measured.

Assays of Enzymatic Activity (Fluorescence Assay)
Apparatuses
    Molecular Devices Spectra MAX GeminiXS
    Corning 96-well non-binding black polystyrene plate
    Heraeus Sepatech Centrifuge
    Mixer, Janke & Kunkel
Materials and Reagents
    Purified Der p 1
    Purified Papain (Car p 1), Sigma
    10 mM Boc-QAR-AMC, Bachem
    10 mM Z-FR-AMC, Bachem
    0.70 mM E-64 in DMF, Merck
    1M DTT, Sigma
    100 mM EDTA, Bie & Berntsen
    50 mM Tris buffer pH 7.0, Sigma
    50 mM Bis-Tris buffer pH 6.5, Sigma
    50 mM Phosphate buffer, Merck
    6.686 mg/mL aluminium hydroxide, Brenntag Biosector
Experimental Procedure Stock solutions of 1M DTT and 100 mM EDTA were made in the beginning of the experimental period, frozen at −20° C., and used through the entire project period. Each day a new buffer was made containing the reducing agent DTT and EDTA from the stock solutions. For a description of assay conditions see table 4. DTT is continuously oxidized by the oxygen in the air and therefore a new buffer must be made each day. To benefit from high-throughput measurements a 96 well microtiter plate was used and each well had an assay volume of 200 µL. The microtiter plate was opaque to avoid cross contamination of emitted fluorescence between wells. The substrate was diluted to the final concentration in the newly made buffer containing DTT and EDTA and transferred to the microtiter plate. The enzyme was diluted in the same buffer and incubated 10 min in the case of papain and 20 min in the case of Der p 1, for their activation. Mixing, transferring and incubation were carried out at room temperature. After incubation the enzyme solution was transferred to the microtiter plate and the measurements were initiated. The measurements were carried out for 10 min with a total of 36 measurements for each well and automatic mixture between each measurement.

TABLE 4

Enzyme assay conditions.

| Variables | Papain | Der p 1 |
|---|---|---|
| Substrate | Z-FR-AMC | Boc-QAR-AMC |
| Inhibitor | E-64 | E-64 |
| DTT | 1-5 mM | 5 mM |
| EDTA | 1-5 mM | 1 mM |
| Buffer | 50 mM Bis-Tris | 50 mM Tris |
| Temperature | 37° C. | 37° C. |
| pH | 6.5 | 7.0 |
| Incubation time, activation | 10 min | 20 min |

The assay volume was not divided equally for each experiment. Thus the specific volumes for enzyme, substrate, buffer and inhibitor were different from experiment to experiment depending on the purpose of the experiment (Table 5).

TABLE 5

Enzyme assay volumes.

| Variables | Activity | Kinetic | Active site titration |
|---|---|---|---|
| Enzyme | 50 µL | 50 µL | 50 µL |
| Substrate | 100 µL | 100 µL | 100 µL |
| Inhibitor | — | — | 50 µL |
| Buffer | 50 µL | 50 µL | — |
| Total | 200 µL | 200 µL | 200 µL |

After measuring the enzymatic activity the maximal slope of the progress curve was estimated using the software Soft-Max® PRO Life Sciences Edition, Molecular Devices, 2001. After estimating the initial velocity of the experiments they were transferred to Prism and analyzed.

IgE Binding Assay

IgE inhibition assay for allergen in solution and for allergen adsorbed and afterwards eluted from an aluminium hydroxide gel adjuvant.

This assay evaluates the capacity that an allergen has to bind IgE from sera of patients allergic to that allergen source. In this context, this assay was used to evaluate the influence of the binding of an allergen to aluminium hydroxide on its ability to bind IgE, and therefore, on its allergenic activity.

Method

IgE inhibition experiments were performed on an ADVIA centaur instrument. Serial dilutions (performed with the TECAN (P-05-07F294)) of the inhibitor (Antigen in solution or antigen gel adjuvant vaccine) were mixed with a fixed amount of biotinylated antigen and further incubated with a solid phase absorbed IgE. The amount of biotinylated allergen bound to the solid phase was estimated as the light emitted after incubation with streptavidin labelled with acridinium ester. The raw data was processed in Excel and transferred to GraphPad Prism v. 4.0 for the final analysis (curve fitting, plotting and statistical comparisons). The data was fitted to a four parameter logistic function:

$$Y = B + \frac{T - B}{1 + 10^{(log_{10}EC50 - log_{10}X)*HillSlope}}$$

and fitted curves was considered parallel if the HillSlope (HS) of the individual fits did not differ significantly.

Experimental Procedure

Due to the nature of aluminium hydroxide it is not possible to evaluate IgE binding in the in the presence of aluminium hydroxide. Therefore the effect of adsorption of Der p 1 to aluminium hydroxide on Der p 1 was evaluated after elution of the Der p 1. A 500 µL sample of 165 µg/mL Der p 1 was incubated with 100 µL 6.868 mg/mL aluminium hydroxide for 1 hour at 4° C. After the adsorption the solution was centrifuged for 5 minutes at 13,000 rpm. The pellet was resuspended in 300 µL 50 mM phosphate buffer and incubated for 2 hours in order to elute the adsorbed Der p 1 from aluminium hydroxide. A 300 µL 165 µg/mL Der p 1 control with no aluminium hydroxide was treated the same way. A Der p extract sample was prepared for incubation with pooled sera IgE.

EXAMPLE 1

Optimization of Substrate and Enzyme 1.1 Substrate Fluorescence

Figure 2A:
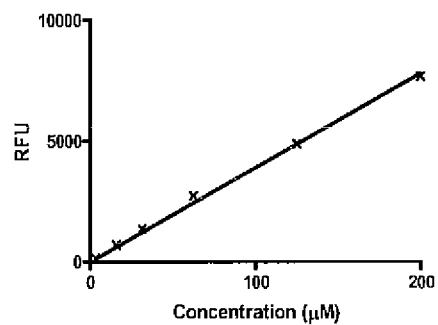
FIG. 2a shows fluorescence of the synthetic substrate Z-FR-AMC and the relationship between fluorescence signal and substrate concentration.

Even though the fluorescence of AMC is quenched while bound to the peptide, some fluorescence can still be measured. The influence of substrate fluorescence on the assay was evaluated by performing fluorescence measurements of substrate at different concentrations. Substrate concentrations from 0 µM to 200 µM were used and endpoint fluorescence was measured (FIG. 2a).

The linear regression that describes the relationship between substrate concentration and fluorescence has a slope of:

$$\beta_1 = 39.07 \pm 1.02 \frac{RFU}{\mu M(Substrate)}$$

This indicates that the fluorescence decreases 39.07 RFU every time one µM of substrate is cleaved. Since one µM substrate produces one µM AMC the increase in fluorescence from produced AMC is 4106 RFU, meaning the net increase in fluorescence, when the substrate is hydrolysed yielding AMC, is:

$$\beta_{net} = 4106 \frac{RFU}{\mu M} - 39.07 \frac{RFU}{\mu M} = 4067 \frac{RFU}{\mu M}$$

Figure 2B:
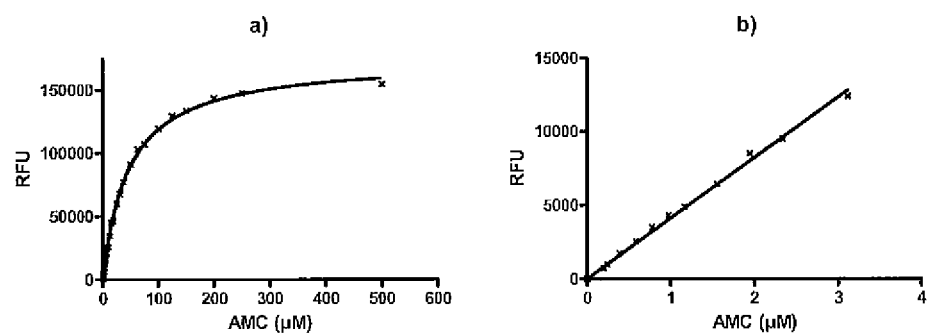
FIG. 2b shows AMC standard curves: a) AMC standard curve up to 500 µM AMC and b) linear range of a).

All fluorescence measurements were converted into a concentration of produced AMC, after the standard curve presented in FIG. 2b.

1.2 Concentrations of Enzyme and Substrate

Figure 3:
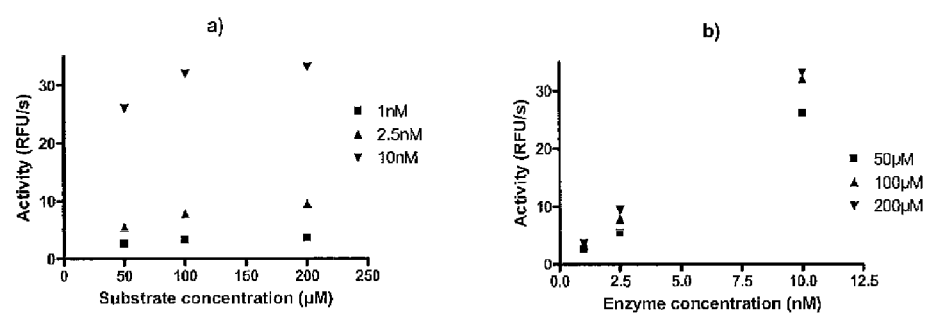
FIG. 3 shows a study of the optimal enzyme and substrate concentration where a) shows activity as a function of substrate concentration and b) shows activity as a function of enzyme concentration.

Preliminary studies of optimal enzyme and substrate concentration for the enzyme activity assay were performed. All experiments were carried out with 1 mM DTT and 5 mM EDTA in assay concentrations. From the literature papain should be present in nM range and the substrate in µM range, depending on the substrate (Schulz et al.; A Sensitive Fluorescent Assay for Measuring the Cysteine Protease Activity of Der p 1, a Major Allergen From the House Dust Mite *Dermatophagoides pteronyssinus, Journal of Clinical Pathology: Molecular Pathology*, Vol. 51, pp. 222-224, 1998; John et al.; Functional Effects of the Inhibition of the Cysteine Protease Activity of the Major House Dust Mite Allergen Der p 1 by a Novel Peptide-based Inhibitor, *Clinical and Experimental Allergy*, Vol. 30, pp. 784-793, 2000; Szabelski et. al; Influence of $Me_2SO$ and Incubation Time on Papain Activity Studied Using Fluorogenic Substrates, *Acta Biochamica Polonica*, Vol. 48:4, pp. 995-1002, 2001). To optimize the exact conditions a 3×3 experimental design was used (FIG. 3).

For the 1 nM enzyme concentration the measured signal in RFU/s was approximately equal to the LOQ for the assay (LOQ=2.44 RFU/s). This makes the measurements with 1 nM enzyme very unreliable. For the 2.5 nM papain solution the measurements were at least 2.3 times the LOQ and for the 10 nM papain solution it was 10.6 times. These results support a linear correlation between the activity measurements and the papain concentration (see FIG. 3(b)). The progress curve of the 10 nM papain solution with 200 µM substrate (which gave the highest activity) showed that the RFU did not exceed 15000 until 4 min. This was a reasonable range for the RFU, since the initial velocity is measured over the first two minutes and the correlation between RFU and concentration of AMC is still linear. At the same time the correlation between the substrate concentration and the measured enzyme activity was not linear indicating that the substrate concentrations used in this experiment were greater than the $K_M$. From these results substrate concentrations below 200 µM and papain concentrations of 10 nM were chosen, since the measured activity was at least one order of magnitude greater than the LOQ.

EXAMPLE 2

Preliminary Experiments on Aluminium Hydroxide Adsorption 2.1 Protein Quantification in the Presence of Aluminum Hydroxide To establish whether it was possible to determine the protein concentration by absorption spectroscopy in a sample containing aluminium hydroxide, absorption measurements of papain in the presence and absence of aluminium hydroxide were carried out.

Figure 4:
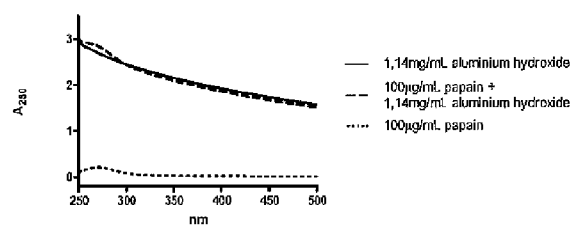
FIG. 4 shows $A_{280}$ of 100 µg/mL papain±1.14 mg/mL aluminium hydroxide and 1.14 mg/mL aluminium hydroxide alone.

The absorbance of the samples containing aluminium hydroxide displayed a high level of light scattering, which was expected given the turbidity of the solution (FIG. 4). Since dilution of the sample results in protein concentrations lower than the limit of quantification this method is not valid for protein estimation under the given conditions. Therefore protein concentration in an aluminium hydroxide containing sample was determined indirectly, by subtracting the amount of protein not bound to aluminium hydroxide (in the liquid phase) from the amount of protein in the control preparation (in the absence of aluminium hydroxide).

2.2 Sedimentation of Aluminium Hydroxide

Figure 5:
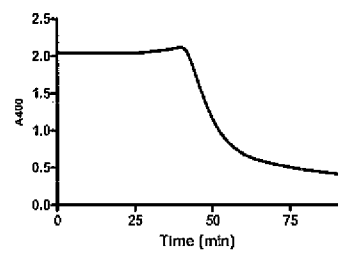
FIG. 5 shows the sedimentation time course of 1.14 mg/mL aluminium hydroxide.

To investigate whether the aluminium hydroxide sediments during the time span of the enzymatic assay, sedimentation was measured as $A_{400}$ over time. The gravitational sedimentation profile showed a threshold of sedimentation at 40 min (FIG. 5). Since the enzymatic assay is completed in 10 min, sedimentation does not occur in the assay.

EXAMPLE 3

Assay Components

In order to verify whether assay components adsorbed to aluminium hydroxide, thereby affecting the result of the enzymatic assay, the following binding experiments were carried out (Table 6).

TABLE 6

Overview of methods used to evaluate the influence of aluminium hydroxide on the assay components.

| Measurement | AMC | Z-FR-AMC | Boc-QAR-AMC | E-64* |
|---|---|---|---|---|
| End point | X | X | X | |
| Activity | | X | X | X |

*E-64 did not show any distinct absorption of light between 200 nm and 900 nm.

All the enzymatic assays describing possible interactions with aluminium hydroxide were carried out with papain, at a final concentration of 5 nM. EDTA was added at 1 mM, and DTT at 5 mM final concentrations. The aluminium hydroxide concentration was 1.14 mg/mL. Since absorption measurement of 1.14 mg/mL aluminium hydroxide displays a high level of light scattering, end point measurements are only carried out on samples without aluminium hydroxide. For all experiments concerning influence of aluminium hydroxide on assay components adsorption to aluminium hydroxide was carried out for 15 min, 30 min, and 60 min.

3.1 AMC

Figure 6:
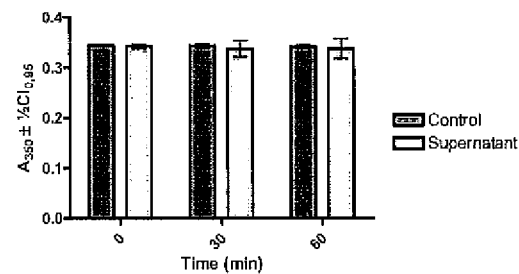
FIG. 6 shows the effect of aluminium hydroxide on AMC. $A_{350}$ of a control sample was compared to $A_{350}$ of a supernatant sample.

It was evaluated whether AMC, the assay product, adsorbs to aluminium hydroxide with time. Triplicate $A_{350}$ measurements of AMC were carried out in a control without aluminium hydroxide and in a supernatant sample, or liquid phase (FIG. 6) on time. The supernatant is obtained from an adsorption experiment where 2 µM AMC in 1.14 mg/mL aluminium hydroxide were mixed together, and then the solid phase fraction was separated from the liquid phase by centrifugation for 5 minutes at 13,000 rpm. A two-way ANOVA of the results showed that the two factors, absorbance and time (p-value=0.40 and p-value=0.066, respectively), had no significant effect on the results. The interaction term between factors (p-value=0.70) showed no significant effect. Thus AMC did not adsorb significantly to aluminium hydroxide under the given conditions for a time period up to one hour.

Figure 7:
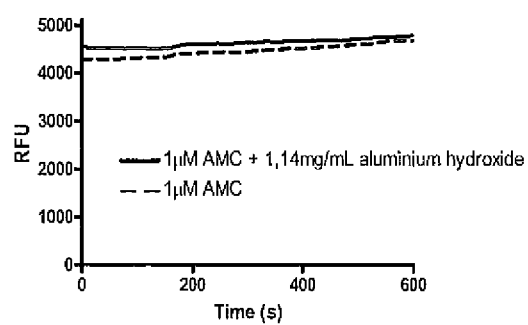
FIG. 7 shows a time study of AMC in the presence and absence of aluminium hydroxide.

To address whether the presence of aluminium hydroxide quenched the fluorescence of AMC an experiment was conducted where the fluorescence of 1 µM AMC was measured with and without aluminium hydroxide, with time. This indicated that no quenching occurred during the time of the assay (FIG. 7). This AMC concentration is equivalent to the enzymatic assay AMC concentration generated by papain and Der p 1.

3.2 Substrates

Figure 8:
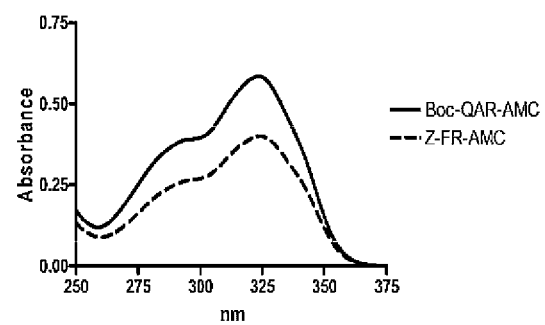
FIG. 8 shows absorbance spectra of the substrates Boc-QAR-AMC and Z-FR-AMC.

It was examined whether the used substrates, Z-FR-AMC and Boc-QAR-AMC, adsorbed to aluminium hydroxide. For such a purpose, the substrates were mixed with 1.14 mg/mL of aluminium hydroxide. The liquid phase (supernatant) was separated from the solid phase by centrifugation. The concentration of substrate in the supernatant was compared to the concentration of substrate in a preparation without aluminium hydroxide (control) with time, in two ways:

a) Comparing the absorption at 325 nm (for both substrates, the maximal absorption occurred at 325 nm (FIG. 8)) in both preparations. Determinations were performed in triplicate, using a substrate concentration of 40 µM (FIGS. 9a and 10a)

b) Measuring the enzymatic activity of papain when mixed with the control in the absence of aluminium hydroxide, the substrate in the presence of aluminium hydroxide (mix) and in the supernatant of the mixture. Determinations were performed in triplicate, using substrate concentrations of 30 µM (FIGS. 9b and 10b)

Figure 9:
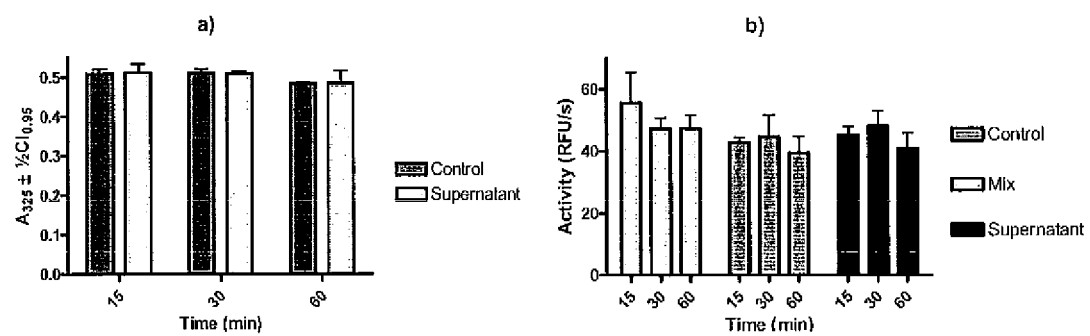
FIG. 9 shows the influence of aluminium hydroxide on the substrate Z-FR-AMC measured as a) $A_{325}$ endpoint measurement and b) papain activity measurement.
Figure 10:
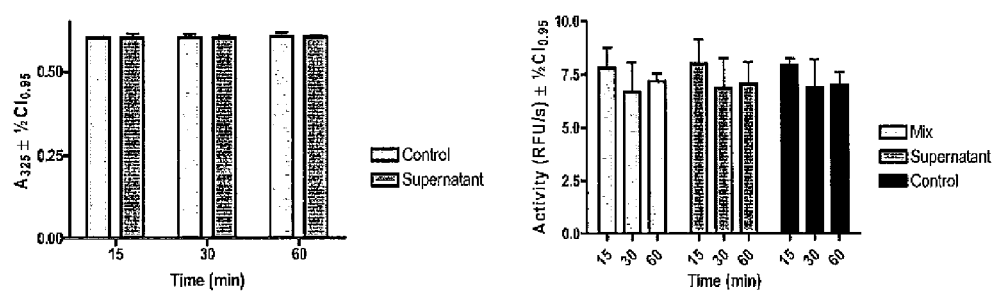
FIG. 10 shows the influence of aluminium hydroxide on the substrate Boc-QAR-AMC measured as a) $A_{325}$ endpoint measurement and b) papain activity measurement.

A two-way ANOVA of the absorbance results of Z-FR-AMC indicated that the absorbance factor (p-value=0.88), had no significant effect (FIG. 9a). The time factor (p-value<0.0001) on the other hand had a significant effect on the result. Inspection of the bar diagram however show larger variation at the time point 60 min. When analyzed only for 15 min and 30 min data points, the time factor indeed becomes non-significant (p-value=0.95). This is a reasonable analysis and confirms the validity of the assay setup.

For the activity assay the statistical analysis of the aluminium hydroxide factor was carried out as a one-way ANOVA (FIG. 9b). The reason for excluding the time factor is that independent enzyme preparations were used for each time point, thereby confounding time and enzyme concentration. The one-way ANOVA showed that there was no significant difference between the means of all of the activity results (p=0.11). This further supports the absorbance measurements indicating no adsorption of Z-FR-AMC to aluminium hydroxide.

A two-way ANOVA of the Boc-QAR-AMC absorbance results indicated that neither the absorbance factor (p-value=0.72), the time factor (p-value=0.24), or the interaction factor had any significant effect on the result (FIG. 10a).

For the activity assay the statistical investigation was carried the same way as for Z-FR-AMC by a one-way ANOVA concerning the activity response only (FIG. 10b). The one-way ANOVA showed that there was no significant difference between the means of all of the activity results (p=0.98). This supports the absorbance measurements indicating no adsorption of Boc-QAR-AMC to aluminium hydroxide.

3.3 E-64

To address whether the cysteine protease inhibitor E-64 adsorbed to aluminium hydroxide enzymatic assays were performed on a 12.5 nM E-64 control without aluminium hydroxide, a mix of E-64 and aluminium hydroxide, and a supernatant of the mix, after having being separated from the solid phase by centrifugation. This E-64 concentration does not completely inhibit the enzyme activity. It is therefore possible to evaluate the binding of E-64 to aluminium hydroxide by enzymatic activity.

Figure 11:
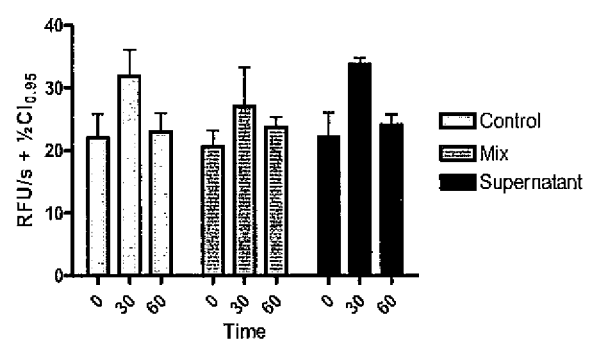
FIG. 11 shows the influence of aluminium hydroxide on papain activity with constant concentration of the cysteine protease specific inhibitor E64.

A one-way ANOVA was performed indicating no significant difference between the means (p-value=0.79), hence no adsorption takes place (FIG. 11). Time points are confounded with enzyme concentration due to separate preparation of enzyme.

3.4 Resume of the Influence of Aluminium Hydroxide on Enzymatic Assay Components In conclusion to the experiments concerning the influence of aluminium hydroxide on enzymatic assay components it was found that aluminium hydroxide does not influence any of the assay components, AMC, Z-FR-AMC, Boc-QAR-AMC, and E-64, in either end-point measurements or enzyme activity measurements.

EXAMPLE 4

4.1 Adsorption of Papain to Aluminium Hydroxide

Figure 12:
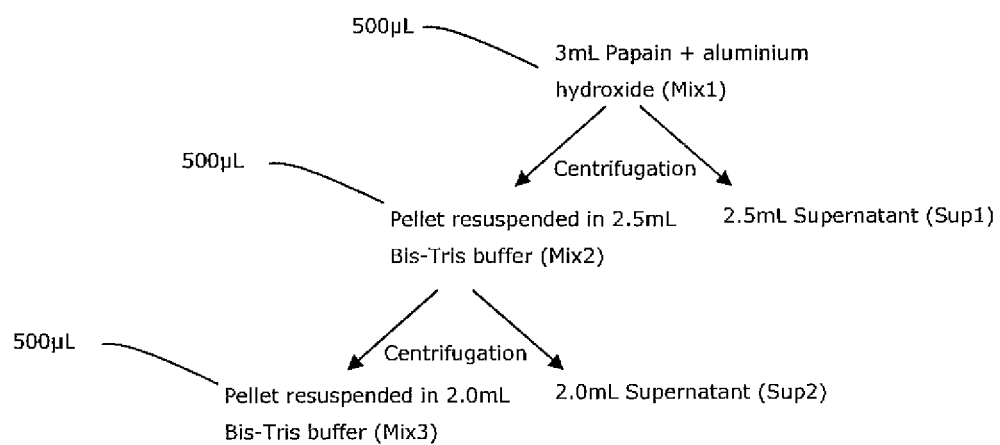
FIG. 12 shows an overview of samples from the adsorption experiment with papain and aluminium hydroxide.

After validation of the enzymatic assay with and without the presence of aluminium hydroxide, an experimental design was made to investigate the kinetic parameters of papain and a possible influence of aluminium hydroxide on them. Since papain was expected to adsorb only in a minor extent to aluminium hydroxide (pI around the PZC of aluminium hydroxide), it was chosen as a negative control. It will reflect the possible effect of the presence of aluminium hydroxide in the assay media on the kinetic results, when the major proportion of the enzyme molecules are not bound to the adjuvant. An overview of the sample preparation is given in FIG. 12.

A 3 mL solution with 100 μg/mL papain and 1.14 mg/mL aluminium hydroxide was prepared. This solution was placed for 1 h at 4° C. to allow adsorption of papain to aluminium hydroxide. After adsorption 500 μL was taken out for further analysis and the rest of the mixture was centrifuged for 10 min at 400 rpm. The rest of the samples analysed follow the flow scheme in FIG. 12. Furthermore a control (Con) containing papain in Bis-Tris buffer in the absence of aluminium hydroxide was prepared. The control was like the aluminium hydroxide mixture incubated for 1 h at 4° C. and analysed afterwards. Samples were Analysed with the Following Methods:
- Determination of protein (enzyme) concentration ($A_{280\,nm}$ and active site titration)
- Enzyme activity measurements 4.2 Determination of Papain Concentration The protein concentration of the different samples was evaluated in two ways:

4.2.1 $A_{280}$

These measurements were converted to protein concentration by the Lambert-Beer's law using a molar absorption coefficient for papain of 2.46 mg/mL. Since it is not technically possible to determine protein concentration from $A_{280}$ in the presence of aluminium hydroxide, the concentration of papain in Mix1 and Mix2 were estimated indirectly. Concentration of protein in Mix1 was the same as in Con, and concentration of protein in Mix2 was the difference between Con and Sup1. An ANOVA of the results showed no difference between Con and Sup1 (p-value=0.615) indicating that papain does not adsorb significantly to aluminium hydroxide. The estimated concentrations of papain in the control and the amount adsorbed to aluminium hydroxide are shown in Table 7.

The protein measurements do not account for all the 100 μg/mL which was the estimated concentration in the Con. The loss of protein might be due to erroneous estimation of the original papain concentration in the stock solution. This concentration was measured by the manufacturer and thus not on the same instrument as the rest of the samples.

TABLE 7

Determination of the kinetic parameters Vmax, Km and kcat (Vmax/protein concentration) as well as protein concentration for papain.

| Preparation | $K_M$ (μM) | Vmax (ng/mL · s) | Protein concentration[a] | $k_{cat}^{a}$ (1/s) | Protein concentration[b] | $k_{cat}^{b}$ (1/s) |
|---|---|---|---|---|---|---|
| Control | 22 | 373.9 | 70.8 ng/mL | 5.13 | 33.7 ng/mL | 11.41 |
| Adsorbed | 21 | 44.1 | 3.0 ng/mL* | 14.58 | 3.4 ng/mL | 12.18 |

[a]Protein concentration determined by A280.
[b]Protein concentration determined by active site titration.
*Obtained protein concentrations are determined indirectly (see text) Control represents a preparation of papain in the absence of aluminium hydroxide. Adsorbed refers to a preparation of papain adsorbed to aluminium hydroxide (mix 2).

4.2.2 Active Site Titration

The active site titration was used to estimate the amount of active enzyme in the different samples. This is in contrast to the protein concentration estimated from $A_{280}$ which represents the total protein content of the sample. The assay conditions used are indicated in Table 8 below.

These results show that approximately 7% (Mix3) of the active papain was adsorbed to aluminium hydroxide, while 91% (Sup1+Sup2) was in solution. This is in agreement with the results obtained in the evaluation of enzyme activity in the samples, see section 4.3.1.

4.3 Enzyme Activity

Two types of enzymatic assays were performed: (i) activity measurements using a fixed substrate concentration to evaluate enzyme activity and (ii) Michaelis-Menten kinetic to estimate the kinetic parameters $V_{max}$ and $K_M$.

All activity assays were conducted with BisTris buffer, pH 6.5, 5 mM DTT/, mM EDTA and Z-FR-AMC as substrate. An overview of the different enzymatic assays performed is given in table 8.

TABLE 8

Specifications of enzyme assays for papain adsorption experiment.

| Analysis Parameter | Activity | Michelis-Menten kinetic | Active site titration |
|---|---|---|---|
| Dilution (Con, Mix1, Sup1) | 2048, 1024, 512, 256 | 1024 | 1024 |
| Dilution (Mix2, Sup2, Mix3) | 2048, 1024, 512, 256 | 128 | 128 |
| Substrate concentration | 30 μM | 12.5 μM, 25 μM, 37.5 μM, 50 μM, 75 μM, 100 μM, 125 μM, 150 μM | 30 μM |
| Inhibitor concentration | | | 0.0 nM, 0.25 nM, 0.50 nM, 1.0 nM, 1.5 nm, 2.0 nM, 3.0 nM, 4.0 nM |
| Incubation time with DTT | 10 min | 10 min | 60 min* |

Activity measurements are single combinations of enzyme and substrate in order to evaluate the level of activity in samples. Michaelis-Menten kinetic measurements of enzyme activity with different substrate concentrations are used to estimate Vmax and KM. All measurements were triplicate.
*Incubation with both DTT and E-64.

4.3.1 Evaluation of Enzymatic Activity

The activity measurements were used to quantitatively analyse the amount of papain adsorbed to aluminium hydroxide and the amount freely distributed in the solution. 96% of activity in Mix1 was found in solution (Sup1+Sup2), while 8% of the activity of papain was adsorbed to aluminium hydroxide (Mix3). The activity of the control is 17% lower than the activity of Mix1. This could be due to a loss of activity of the protein in the control during the time span of the experiment. This loss was prevented by the presence of aluminium hydroxide.

In order to further evaluate this observation, new experiments were conducted where the activity of papain was followed over time in the absence of aluminium hydroxide. Papain was mixed with 50 mM Bis-Tris buffer to a final concentration of 10 μg/mL in a total volume of 500 μL. The mixture was incubated at 4° C. and samples were taken out at 0, 30 and 60 min. The samples were diluted and incubated for 10 min in buffer containing DTT and subsequently activity was measured after addition of substrate. The results analysed with one-way ANOVA showed that there was a significant difference between the 3 time points (p-value=0.015) and by Newman-Keuls comparison test 60 min was found to differ from the other two time points, and was 7% lower. These results suggest that during the 60 min of incubation between papain and aluminium hydroxide, papain in the control sample has lost 7% of its activity. Additional loss occurs until the initiation of the enzymatic assay.

4.3.2 Michaelis-Menten Kinetic Parameters

The Michaelis-Menten parameters $K_M$ and $V_{max}$ were evaluated in the different samples.

The estimated values of $K_M$ and $V_{max}$ from the different samples are shown in table 7 above. Bartlett's test indicated no significant difference between sample variances of the $K_M$ (p-value=0.758) and a one-way ANOVA was used to compare means. The one-way ANOVA test showed no significant difference between $K_M$ estimates (p-value=0.999), indicating that the affinity towards the substrate does not change when papain is in the presence and absence of aluminium hydroxide.

$V_{max}$ in solution (Sup1+Sup2) is 97% of that in Mix1, while $V_{max}$ in Mix3 corresponds to a 7%.

$V_{max}$ is specific for a defined enzyme and is linearly dependent on the enzyme concentration in the assay. The normalization of $V_{max}$ by the enzyme concentration, gives the parameter $k_{cat}$, which is only dependent on the characteristics of the enzyme activity. Table 7 above shows the estimated values of $k_{cat}$ for the different samples, calculated from the enzyme concentration values obtained from active site titration and $A_{280}$.

The values of $k_{cat}$ obtained from $A_{280}$ determination of protein concentration were approximately half of those obtained with active site titration in the control, indicating that half of the protein in the samples was inactive. The $k_{cat}$ values of Con, Mix1, Sup1, Mix2, and Mix3 are comparable when the enzyme concentration was calculated by active site titration, suggesting that the presence of aluminium hydroxide does not affect the kinetic properties of papain. The $k_{cat}$ values of Con, Mix1, Sup1, and Sup2 are also comparable when the enzyme concentration is calculated from $A_{280}$. However the indirect determination of protein concentration in Mix2 renders the $k_{cat}$ value more imprecise.

The fact that the kinetic parameters evaluated in the presence and absence of aluminium hydroxide are not significantly different indicates that the presence of aluminium hydroxide did not affect the enzymatic reaction. In conclusion, these results show that it it's possible to measure the enzymatic properties of an enzyme in the presence of aluminium hydroxide, when the major part of the enzyme (93%) is not bound to the adjuvant.

EXAMPLE 5

5.1 Adsorption of Der p 1 to Aluminium Hydroxide

According to the theory of adsorption of proteins to aluminium hydroxide, Der p 1 was expected to adsorb (pI below the PZC of the aluminium hydroxide). The effect of this adsorption on Der p 1 activity and structure were examined.

Figure 13:
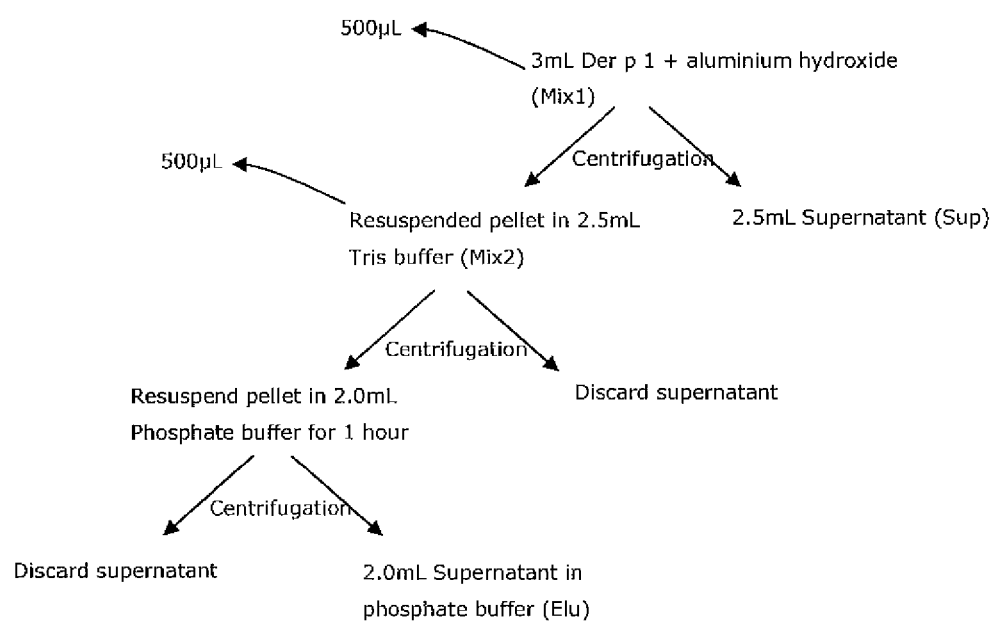
FIG. 13 shows an overview of samples from the adsorption experiment with Der p 1 and aluminium hydroxide.

An overview of the sample preparation is given in FIG. 13. A 3 mL solution with 100 μg/mL Der p 1 and 1.14 mg/mL aluminium hydroxide was prepared. This solution was placed for 1 h at 4° C. to allow adsorption of Der p 1 to aluminium hydroxide. After adsorption 500 μL was taken out for further analysis and the rest of the mixture was centrifuged for 10 min at 4000 rpm. An elution step was performed for 1 h at 4° C. where the pellet of Mix2 was resuspended in phosphate buffer. Furthermore two controls (Con1 and Con2) containing Der p 1 in Tris buffer in the absence of aluminium hydroxide were prepared. Con1 was analyzed in the beginning of the experiment and Con2 was analyzed at the end of the 2 hours experiment.

Samples were Analysed with the Following Methods:
Determination of protein concentration ($A_{280\ nm}$ and RIE)
Enzyme activity measurements
IgE binding

5.2 Determination of Der p 1 Concentration

The determination of Der p 1 concentration in the different samples was evaluated by $A_{280}$ and RIE.

5.2.1 $A_{280}$

In order to quantify protein content absorbance at 280 nm was measured on samples without aluminium hydroxide (Con1, Con2, Sup, and Elu). The absorbance measurements were converted to protein concentration by the Lambert-Beer's law using a molar absorption coefficient for Der p 1 of 1.72 mg/mL as shown in table 8a.

TABLE 8a

Determination of the kinetic parameters Vmax, Km and kcat (Vmax/protein concentration) as well as protein concentration for Der p1

| Preparation | $K_M$ (μM) | Vmax (ng/mL · s) | Protein concentration[a] | $k_{cat}$[a] (1/s) | Protein concentration[c] | $k_{cat}$[c] (1/s) |
|---|---|---|---|---|---|---|
| Control | 47 | 0.25 | 10.4 | 0.024 | 13.9 | 0.018 |
| Adsorbed | 56 | 0.15 | 7.1* | 0.022 | 7.8 | 0.019 |
| Eluted | 51 | 0.11 | 4.0 | 0.025 | 7.6 | 0.014 |

[a]Protein concentration determined by A280.
[c]Protein concentration determined by RIE.
*Obtained protein concentrations are determined indirectly (see text) Control represents a preparation of Der p 1 in the absence of aluminium hydroxide. Adsorbed refers to a preparation of Der p 1 adsorbed to aluminium hydroxide (mix 2).

Concentration of protein in Mix1 and Mix2 were estimated indirectly. The protein concentration in Mix1 was considered the same as in Con1 and the protein concentration in Mix2 was the difference between Con1 and Sup. A t-test showed no significant difference between the protein concentration in Con1 and Con2 (p-value=0.092). 32% of the protein content in Con1 was found in Sup, indicating an adsorption degree of approximately 70%. From the adsorbed protein, 56% was eluted from aluminium hydroxide using phosphate buffer.

5.2.2 RIE

Another method applied to quantify protein content was RIE. The samples Con1, Con2, Sup, and Elu were evaluated together with three Der p 1 standards (125 ng, 250 ng, and 500 ng). The estimated Der p 1 concentrations of Der p 1 in the control, the amount adsorbed to aluminium hydroxide as well as the amount eluted are shown in table 8a.

The estimated values were generated from the linear regression standard curve of the three standards (concentration as a function of area of precipitate). 44% of the protein content in Con1 was found in Sup indirectly indicating an adsorption degree of approximately 56%. From the adsorbed protein 98% was eluted from aluminium hydroxide using phosphate Buffer. The concentration of the Con1 and Con2 was outside the prediction area of the standard curve, and it is therefore likely that the Der p 1 concentration is underestimated. This can explain the high elution degree of Der p 1 from aluminium hydroxide, since the adsorbed Der p 1 concentration is estimated as the difference between Con1 and Sup.

5.3 Enzyme Activity

Different types of enzymatic assays were performed: (i) activity measurements using a fixed substrate concentration to evaluate enzyme activity, and (ii) Michaelis-Menten kinetic to estimate the kinetic parameters $V_{max}$ and $K_M$.

All activity assays were conducted with Tris buffer, pH 7.0, 5 mM DTT, 1 mM EDTA and Boc-QAR-AMC as substrate. An overview of the different enzymatic assays performed is given in table 9.

TABLE 9

Specifications of enzyme assays for Der p 1 adsorption experiment.

| Analysis Parameter | Activity measurement | Michelis-Menten kinetic |
|---|---|---|
| Dilution (Con1, Mix1, Sup, Mix2, Elu, Con2) | 4 and 8 | 8 |
| Substrate concentration | 100 μM | 25 μM, 50 μM, 75 μM, 100 μM, 150 μM, 200 μM |
| Inhibitor concentration | | |
| Incubation time | 20 min | 20 min |

Activity measurements are single combinations of enzyme and substrate in order to evaluate the level of activity in samples. Michaelis-Menten kinetic measurements of enzyme activity with different substrate concentrations are used to estimate Vmax and KM. All measurements were triplicate.
*Incubation with both DTT and E-64.

5.3.1 Evaluation of Enzymatic Activity

Figure 14:
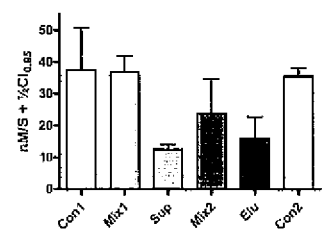
FIG. 14 shows Der p 1 activity of different samples in the presence and absence of aluminium hydroxide.

The activity measurements of Der p 1 in the absence and presence of aluminium hydroxide were used to quantify the amount of Der p 1 adsorbed to aluminium hydroxide and the amount freely distributed in the solution. The results of the activity measurements are summarized in FIG. 14.

The activity of the non adsorbed Der p 1 in Sup corresponds to 33% of the activity in Mix1. 66% of the activity of Der p 1 was adsorbed to aluminium hydroxide and 67% of this activity was desorbed after elution from Mix2 with phosphate buffer.

In order to monitor the stability of Der p 1 during the experiment period, the activity of Con1 was measured at the beginning of the experiment and Con2 at the end. Performance of a one-way ANOVA on Con1, Con2, and Mix1 showed no significant difference between the means (p-value=0.76). This indicates that neither time nor presence of aluminium hydroxide influences the activity of Der p 1 under these conditions.

5.3.2 Michaelis-Menten Kinetic Parameters

The Michaelis-Menten parameters $K_M$ and $V_{max}$ were evaluated in the different samples.

Figure 15:
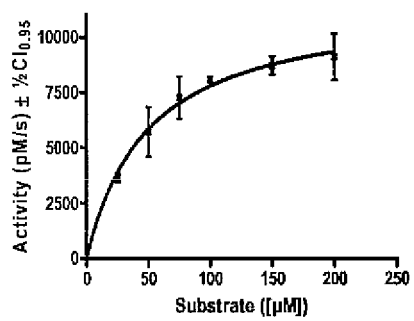
FIG. 15 shows an Michaelis-Menten curve for Der p 1 in the presence of aluminum hydroxide.

FIG. 15 shows a typical Michaelis-Menten curve for Der p 1 in the presence of aluminium hydroxide. The values of $K_M$ and $V_{max}$ are shown in table 8a. Bartlett's test indicated no significant difference between the variances of the $K_M$ (p-value=0.11) and a one-way ANOVA showed no significant difference between the means of the samples (p-value=0.62). This indicates that the affinity of Der p 1 towards Boc-QAR-AMC does not change in the presence of aluminium hydroxide.

$V_{max}$ of Con2 is 14% lower than $V_{max}$ in Con1 (t-test, p-value=0.0024) indicating that Der p 1 had lost activity during the time period of the experiment. A Newman Keuls multiple comparison test showed no significant difference between $V_{max}$ of Con1 and Mix1 (p>0.05), suggesting that aluminium hydroxide had no influence on Der p 1 activity. Furthermore it seems that aluminium hydroxide has prevented the loss of activity in time observed from Con1 to Con2. $V_{max}$ in Sup and Mix2 is 30% and 62% of $V_{max}$ in Mix1, respectively. 68% of the activity in Mix2 was found in Elu.

The $k_{cat}$ values of Der p 1 were estimated from the obtained $V_{max}$ values and the protein concentrations obtained from the different methods ($A_{280}$, and RIE) as shown in table 8a, $k_{cat}$ values from the different samples are comparable when the protein concentration was estimated by $A_{280}$ and RIE.

In conclusion the obtained $K_M$ and $k_{cat}$ values for Der p 1 were not significantly different in the absence of aluminium hydroxide and when the major part of the Der p 1 molecules (60-70%) are adsorbed to the aluminium hydroxide. These data supports that it is possible to measure the enzymatic activity of an enzyme adsorbed to aluminium hydroxide making an evaluation of the impact that the adsorption of an enzyme to aluminium hydroxide has on the activity/structure of the enzyme possible.

5.4 IgE Binding

The influence of aluminium hydroxide on the ability of Der p 1 in the absence of aluminium hydroxide (Con 1) and of Der p 1 bound and eluted from aluminium hydroxide (Elu) to bind IgE from sera of HDM allergic patients was evaluated.

Figure 16:
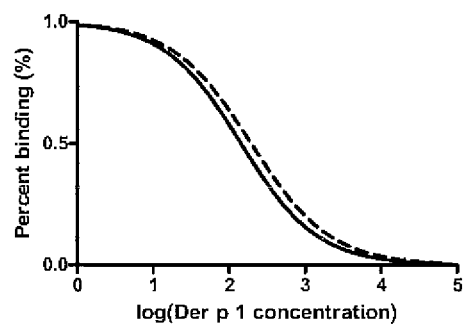
FIG. 16 shows inhibition of IgE binding. Discontinous line: Der p 1 eluted from aluminium hydroxide (Elu), continuous line: Control Der p 1 in the absence of aluminium hydroxide (Con 1)

The inhibition of the signal from biotin labelled standard Der p 1 using increasing concentrations of Der p 1 in the Con1 and Elu under evaluation followed a sigmoidal downhill curve (FIG. 16).

Comparing the curve of Con1 with Elu it is evident that the bottom levels are identical therefore complete inhibition is possible in either case. This indicates that all IgE epitopes in Con1 were still present in Elu. A one sample t-test comparing the Hill slopes of Con1 and Elu showed that the means were not significantly different (p=0.83), which indicates that the affinity of IgE towards epitopes on Der p 1 was conserved upon binding to aluminium hydroxide

The invention claimed is:

1. A method of measuring the immunological activity of Der p 1 in a immunogenic preparation comprising the allergenic enzyme Der p 1 and optionally one or more further allergenic enzyme(s) and an oxygen-containing metal salt adjuvant, wherein the preparation is in the form of a mixture comprising a liquid phase and a solid phase, and wherein at least a part of the allergenic enzyme(s) is adsorbed to the solid phase, the method comprising the steps of measuring the enzymatic activity of Der p 1 in the mixture, and/or measuring the enzymatic activity of Der p 1 in the liquid phase upon a separation of the liquid phase from the solid phase, and/or measuring the enzymatic activity of Der p 1 in the solid phase upon a separation of the liquid phase from the solid phase, in an enzyme activity assay wherein Z-Leu-Leu-Glu-MCA is used as a specific substrate for measuring the enzymatic activity of Der p 1, and using the measurement obtained as an indication of the immunological activity of the preparation, wherein the oxygen-containing metal salt adjuvant is aluminum hydroxide.

2. A method for quantification of the amount of Der p 1 in an immunogenic preparation comprising the allergenic enzyme Der p 1 and optionally one or more further allergenic enzyme(s) and an oxygen-containing metal salt adjuvant, wherein the preparation is in the form of a mixture comprising a solid phase and a liquid phase, and wherein at least a part of the allergenic enzyme(s) is adsorbed to the solid phase, the method comprising the steps of measuring the enzymatic activity of Der p 1 in the mixture, and/or measuring the enzymatic activity of Der p 1 in the liquid phase upon a separation of the liquid phase from the solid phase, and/or measuring the enzymatic activity of Der p 1 in the solid phase upon a separation of the liquid phase from the solid phase, in an enzyme activity assay wherein Z-Leu-Leu-Glu-MCA is used as a specific substrate for measuring the enzymatic activity of Der p 1, and using the measurement obtained for quantifying the amount of allergenic enzyme, wherein the oxygen-containing metal salt adjuvant is aluminum hydroxide.

3. The method according to claim 1, wherein an inhibitor is used to inhibit the allergenic enzyme Der p 1 in the preparation.

4. The method according to claim 1, wherein the allergenic enzyme(s) is in the form of an extract.

5. The method according to claim 1, wherein the inhibitor used is selected from the group consisting of E64 (L-trans-epoxysuccinyl-L-leucylamido (4- guanidino) butane) and other epoxides.

6. The method according to claim 5, wherein the inhibitor used is E64.

7. The method according to claim 1, wherein the one or more further allergenic enzyme(s) is one or more selected from the group consisting of Der p 3 Der p 6 and Der p 9.

8. The method according to claim 1, wherein the preparation comprises one or more further allergens not having enzymatic activity.

9. The method according to claim 1, wherein the enzyme activity assay is an absorbance assay, fluorescence assay, FTIR or an immunological method.

10. The method according to claim 9, wherein the enzyme activity assay is an ELISA.

11. The method according to claim 9, wherein the enzyme activity assay is a fluorescence assay.

12. The method according to claim 1, wherein the preparation is subjected solely to a measurement of the enzymatic activity of the allergenic enzyme Der p 1 in the mixture of the liquid phase and the solid phase (measurement 1).

13. The method according to claim 1, wherein the preparation is subjected solely to a measurement of the enzymatic activity of the allergenic enzyme Der p 1 in the liquid phase upon a separation of the liquid phase from the solid phase (measurement 2).

14. The method according to claim 1, wherein the preparation is subjected solely to a measurement of the enzymatic activity of the allergenic enzyme Der p 1 in the solid phase upon a separation of the liquid phase from the solid phase (measurement 3).

15. The method according to claim 1, wherein, the preparation is subjected both to a measurement of the enzymatic activity of the allergenic enzyme Der p 1 in the mixture of the liquid phase and the solid phase (measurement 1), and to a measurement of enzymatic activity of the allergenic enzyme Der p 1 in the liquid phase (measurement 2).

16. The method according to claim 1, wherein the preparation is subjected both to a measurement of the enzymatic activity of the allergenic enzyme Der p 1 in the liquid phase (measurement 2), and to a measurement of the enzymatic activity of the allergenic enzyme Der p 1 in the solid phase (measurement 3).

17. The method according to claim 1, wherein the enzymatic activity of a solution comprising the allergenic enzyme Der p 1 is used for preparing the adjuvanted preparation is measured, and the measurement for the said solution is compared to the measurement obtained for the adjuvanted preparation in order to evaluate the effect on the immunological activity of the preparation of the adjuvanted preparation.

18. The method according to claim 1, wherein the preparation is subjected to the enzymatic activity measurement immediately after preparation and after one or more periods of storage, and the indication of the immunological activity of the preparation is based on a comparison of the former and latter measurements.

19. The method according to claim 1, wherein the indication of the immunological activity of the preparation is based on a comparison of the measurement obtained for the adjuvanted preparation and prior corresponding measurements of the same type of adjuvanted preparation or of another type of preparation.

20. The method according to claim 13, wherein the separation process is performed by centrifugation, extraction or simple sedimentation.

21. The method according to claim 20, wherein the separation process is performed by centrifugation.

22. The method according to claim 1, wherein the immunological activity is the ability to elicit an IgG-mediated immune response.

23. The method according to claim 1, wherein the immunological activity is the ability to elicit an IgE-mediated immune response.

24. The method according to claim 2, wherein the one or more further allergenic enzyme(s) is one or more selected from the group consisting of Der p 3, Der p 6 and Der p 9.

25. The method according to claim 2, wherein the preparation is subjected solely to a measurement of the enzymatic activity of the allergenic enzyme Der p 1 in the mixture of the liquid phase and the solid phase (measurement 1).

26. The method according to claim 2, wherein the preparation is subjected solely to a measurement of the enzymatic activity of the allergenic enzyme Der p 1 in the liquid phase upon a separation of the liquid phase from the solid phase (measurement 2).

27. The method according to claim 2, wherein the preparation is subjected solely to a measurement of the enzymatic activity of the allergenic enzyme Der p 1 in the solid phase upon a separation of the liquid phase from the solid phase (measurement 3).

28. The method according to claim 2, wherein, the preparation is subjected both to a measurement of the enzymatic activity of the allergenic enzyme Der p 1 in the mixture of the liquid phase and the solid phase (measurement 1), and to a measurement of enzymatic activity of allergenic enzyme in the liquid phase (measurement 2).

29. The method according to claim 2, wherein the preparation is subjected both to a measurement of the enzymatic activity of the allergenic enzyme Der p 1 in the liquid phase (measurement 2), and to a measurement of the enzymatic activity of the allergenic enzyme Der p 1 in the solid phase (measurement 3).

* * * * *